(12) United States Patent
Horsman et al.

(10) Patent No.: US 7,686,959 B2
(45) Date of Patent: Mar. 30, 2010

(54) CONTROL SYSTEM AND METHOD FOR FLASH SEPARATION

(75) Inventors: Jeffrey A. Horsman, Charlottesville, VA (US); John R. Bickler, Hampstead, NC (US)

(73) Assignee: Biotage AB, Charlottesville, VA (US)

( * ) Notice: Subject to any disclaimer, the term of this patent is extended or adjusted under 35 U.S.C. 154(b) by 1042 days.

(21) Appl. No.: 11/384,511

(22) Filed: Mar. 21, 2006

(65) Prior Publication Data

US 2006/0219633 A1  Oct. 5, 2006

Related U.S. Application Data

(63) Continuation-in-part of application No. 10/840,450, filed on May 5, 2004, now abandoned.

(60) Provisional application No. 60/735,172, filed on Nov. 10, 2005.

(51) Int. Cl.
*B01D 15/08* (2006.01)
(52) U.S. Cl. .................. 210/656; 210/143; 210/198.2
(58) Field of Classification Search ............... 210/635, 210/656, 659, 143, 198.2; 436/161, 518
See application file for complete search history.

(56) References Cited

U.S. PATENT DOCUMENTS

| | | | | |
|---|---|---|---|---|
| 4,066,879 A * | 1/1978 | Leaver et al. | ................ | 700/265 |
| 4,468,331 A * | 8/1984 | Antle et al. | .................. | 210/659 |
| 4,478,713 A * | 10/1984 | Girot et al. | .................. | 210/101 |
| 4,579,663 A * | 4/1986 | Poile et al. | ................... | 210/656 |
| 4,592,842 A * | 6/1986 | Tomlinson | ................... | 210/659 |
| 4,719,017 A * | 1/1988 | Uchino et al. | ................ | 210/656 |
| 4,802,981 A * | 2/1989 | Kenney et al. | ........... | 210/198.2 |
| 5,203,992 A * | 4/1993 | Drouen | ................... | 210/198.2 |
| 5,209,853 A * | 5/1993 | Lynch et al. | ................. | 210/656 |
| 5,695,760 A * | 12/1997 | Faanes et al. | ............ | 424/178.1 |
| 5,958,246 A * | 9/1999 | Tipler et al. | .................. | 210/656 |
| 6,139,733 A | 10/2000 | Hargro et al. | | |
| 6,221,252 B1 | 4/2001 | Hargro et al. | | |
| 6,294,087 B1 | 9/2001 | Hargro et al. | | |
| 6,413,431 B1 * | 7/2002 | Abedi | ........................... | 506/6 |
| 6,436,284 B1 | 8/2002 | Leavesley et al. | | |
| 6,652,746 B2 | 11/2003 | Michel et al. | | |

(Continued)

FOREIGN PATENT DOCUMENTS

JP    3423707    7/2003

OTHER PUBLICATIONS

Snyder, Introduction to Modern Liquid Chromatography, John Wiley, 1979, pp. 663-686.*

*Primary Examiner*—Ernest G Therkorn
(74) *Attorney, Agent, or Firm*—Harness, Dickey & Pierce, P.L.C.

(57) ABSTRACT

Provided are methods and apparatus for determining conditions for performing chromatography, particularly flash chromatography. The methods may be utilized for separating compounds in a sample in a column chromatography system. The method includes determining at least two retention factors corresponding to the TLC performance of a target compound and an adjacent compound and defining a sample loading amount and a solvent gradient profile using at least two solvents that will result in differential elution of the target and adjacent compounds from a chromatography column. The chromatography system and loading parameters may be selected to provide satisfactory separation of the target compound from adjacent compounds.

20 Claims, 11 Drawing Sheets

U.S. PATENT DOCUMENTS

| | | |
|---|---|---|
| 6,790,361 B2 | 9/2004 | Wheat et al. |
| 6,802,967 B2 | 10/2004 | Masuda et al. |
| 6,802,969 B2 | 10/2004 | Tanimura |
| 7,169,308 B2 * | 1/2007 | Ohkura ........................ 210/656 |
| 2005/0247625 A1 * | 11/2005 | Liu et al. .................... 210/635 |
| 2008/0047899 A1 * | 2/2008 | Davison et al. ............. 210/656 |

* cited by examiner

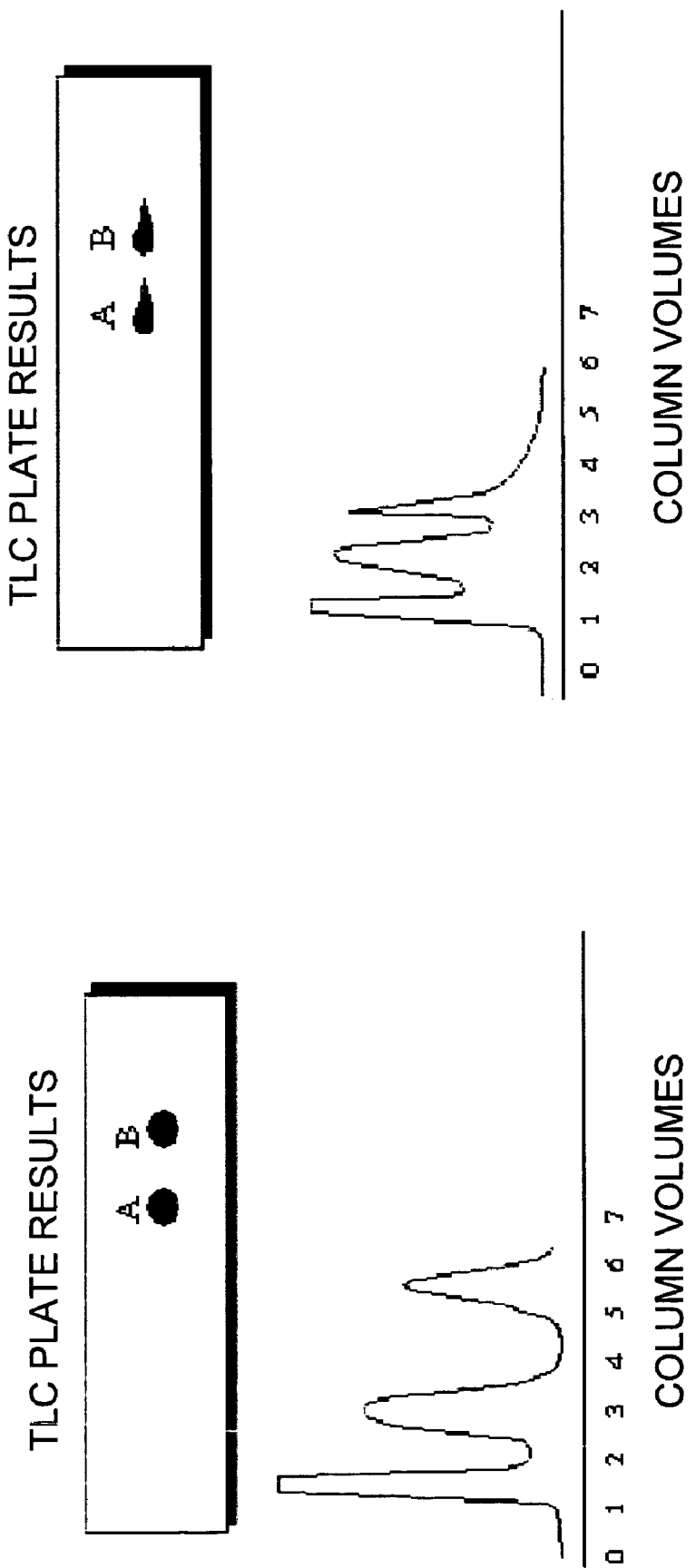

CONTROL SYSTEM AND METHOD FOR FLASH SEPARATION

PRIORITY STATEMENT

This application is a continuation-in-part of U.S. patent application Ser. No. 10/840,450, now abandoned and now published as U.S. Patent Application Publication No. 2005/0247625, filed May 5, 2004, and also claims priority under 35 U.S.C. § 119 from U.S. Provisional Patent Application No. 60/735,172, which was filed Nov. 10, 2005, the disclosures of which are incorporated herein by reference to the fullest extent consistent with the present disclosure.

BACKGROUND OF THE INVENTION

The invention described below relates to chromatography and, more particularly, to chromatography systems and methods of configuring and operating such chromatography systems for improving the separation of various components found within a composition.

Chromatography generally involves the use of one or more solvents to separate a sample composition of multiple components into individual components as a result of the solvents and the sample composition flowing around, over, or through a stationary liquid or solid phase. Different mechanisms and/or techniques may be used to perform different types of chromatography. For example, thin layer chromatography (TLC) generally involves the use of a vessel containing a solvent or solvent system and a chromatography plate ("the plate") that includes a thin layer of silica or other suitable material. In conventional TLC, a sample composition is applied to a lower portion of the plate and a lower edge of the plate is immersed in a solvent composition. The plate is then maintained in a generally vertical orientation so that over time the solvent will move, via capillary action, upwardly through the layer of material provided on the surface of the plate. As the solvent moves past the sample composition, one or more of the components within the sample will be dissolved and carried along with the solvent upwardly along the surface of the plate. The various components will be moved by the solvent at different rates, thereby tending to separate a plurality of components across the surface of the TLC plate.

Based on the relative distances between the movement of the solvent front, $L_{SF}$, and the movement of the various dissolved components A, B . . . N that were present in the sample composition, $L_{CA}, L_{CB} \ldots L_{CN}$, across the plate within a given period of time, a corresponding retention factor ($R_f$) may be calculated for each of the separated or distinguishable components. The $R_f$ represents the ratio of the distance traveled by a component present in the sample and the solvent. For example, if component A of a sample is moved a distance $L_{CA}$ by a solvent that traveled a distance $L_{SF}$ along the plate at the same time, the $R_f$ for component A may be calculated using equation 1:

$$L_{CA}/L_{SF} = R_{fA} \qquad (1).$$

Because various chromatographic techniques provide different combinations of advantages and disadvantages, those skilled in the art of chromatography may use multiple chromatographic techniques and/or methods in order to achieve an acceptable separation of the components within a single sample composition. However, the separation conditions that produce acceptable results for one chromatographic method may not, and commonly will not, produce acceptable results if transferred directly to another chromatographic method. Accordingly, the process of adapting the separation conditions used in one type of chromatography to another type of chromatography has continued to challenge those skilled in the art and typically requires additional experimentation to adapt the initial separation conditions in order to achieve satisfactory results.

Although various methods, approaches and techniques have been developed for use in such efforts and have proved helpful to chemists, pharmacists and others who practice such chromatography, a significant degree of operator involvement remains in most instances. As will be appreciated by those skilled in the art, the degree of operator involvement, including, for example, calculations and "guess and check" trials for improving the separation of a particular group of components may be increased when dealing with unknown components and/or components that exhibit similar $R_f$ values in conventional solvent systems.

SUMMARY OF THE INVENTION

The invention relates to methods and control systems for operating chromatographic apparatus and, in particular the operation of flash separation apparatus using a multi-solvent systems and solvent gradient techniques for achieving improved separation and/or increased efficiency of the chromatographic system.

The basic technique involves separating the various compounds present in a sample using a column chromatography system, typically an automated column chromatography system. The method includes receiving inputs comprising $R_f$ values corresponding to at least a compound of interest, the primary compound, and one or more of the other compounds, the secondary compound(s), present in the sample that exhibit $R_f$ values similar to that of the compound of interest, for example, those compounds that lie on either side or "bracket" the compound of interest on a TLC plate. Other inputs will include the identification and ratios of solvents present in the TLC solvent system used for obtaining the $R_f$ values and the parameters associated with the available chromatography columns. These inputs will, in turn, be used to calculate the gradient profile for use in the column chromatography system, the sizing of the chromatography column and/or the sample loading that may be used with a particular chromatography column while still achieving acceptable separation.

As will be appreciated, the range of inputs for a particular separation will be determined by the relationship of the primary and secondary compounds, the availability and/or suitability of the solvents that can be used to formulate the solvent system, the degree of purity desired and/or the amount of the primary compound that is to be collected. Accordingly, implementing the methods according to the example embodiments of the invention may require inputs including 2 or more retention factors and the solvent ratio and solvent strengths of the solvents included in the solvent system used in the corresponding initial TLC. Additional or alternative inputs may include additional information regarding the suitability or identity of stronger and/or weaker solvents that could be used to modify the degree of separation suggested by the initial TLC data.

The necessary solvent information may be input by the operator and/or may be maintained in a reference table that may be accessed by the control system and/or the operator. Such reference tables may include data relating to solvent strength values for determining or selecting the solvents a stronger solvent among the first and second solvents based on the referenced solvent strength values. The solvent strength values may be relative solvent strength values based on polarity values. The information usable to determine a stronger solvent among the first and second solvents may include an indication of the stronger solvent.

If the input data indicates two or more retention factors, determining a Δcolumn volume (ΔCV) based on the two more or retention factors, and determining a sample mass, a column size, and a flow rate by reference to a data repository including suggested sample masses, column sizes, and flow rates.

These techniques and features according to the example embodiments of the invention may be implemented in a chromatography system that includes a chromatography column connected to receive a sample composition; one or more pumps connected to the chromatography column; one or more valves capable of limiting the ratio of at least a first solvent and a second solvent flowing to the one or more pumps; and a controller operable to perform operations, including, receiving input, generating a gradient profile based on received input, and controlling the pump(s) and valve(s) to separate the sample composition based on the gradient profile.

The inputs into the controller will include at least two retention factors including a first retention factor corresponding to the target compound and at least one other retention factor corresponding to another compound, typically that of the compound(s) having the next higher and/or lower retention factor in the TLC solvent system. Other inputs into the controller will include an indication of the solvents and solvent ratio of the solvent system used to obtain the corresponding retention factors. Using these inputs and, optionally, additional data resident in or accessible by the controller, the controller will generate a gradient profile that includes a starting point and an ending point corresponding to a starting solvent ratio that is less than, and an ending solvent ratio that is greater than, that of the TLC solvent system.

In another example embodiment of the invention, a chromatography system may include a profile generator for generating a gradient profile that includes a gradient portion extending between a starting ratio and an ending ratio of the solvents that comprise the selected solvent system; a chromatography controller that includes a pump controller for controlling one or more pumps, a valve controller for controlling the flow of the solvents through the pumps, a detector controller for detecting compounds present in the effluent of the chromatography system and/or at intermediate points within the chromatography system; and a display for guiding an operator through the initial configuration of the system, indicating the historical, current and/or upcoming operating conditions and/or displaying the results currently being achieved or having previously been achieved.

The example embodiments of the methods and apparatus for determining conditions for chromatography described here may provide one or more advantages including, for example, options for linear, continuous non-linear and/or stepped gradient profiles for two or more solvents that may be automatically generated from corresponding TLC data and solvent data for simplifying and/or automating the transfer of separation conditions from TLC directly to column chromatography with a high degree of confidence, thereby reducing the need for multiple TLC runs. In connection with generating the gradient profile, the controller may access data for distinguishing between weaker and stronger solvents based on solvent strength values and/or polarity values of the solvents utilized in the solvent system, thus relieving the operator from the need to determine which of the solvents should be the majority solvent at the start of a gradient.

Additional details with regard to certain example embodiments of the invention are set forth in the accompanying drawings and the description provided below. Other features and advantages of the invention may be apparent to those skilled in the art from the description and drawings, and from the claims.

BRIEF DESCRIPTION OF THE DRAWINGS

The invention will become more apparent by consideration of the written description below in which example embodiments are detailed with reference to the attached drawings in which:

FIGS. 10A and 10B illustrate the separations achieved using a proper sample loading mass, FIG. 10A, and using excess sample loading mass, FIG. 10B.

These drawings are provided for illustrative purposes only and are not drawn to scale. The spatial relationships and relative sizing of the elements illustrated in the various embodiments may have been reduced, expanded or rearranged to improve the clarity of the figure with respect to the corresponding description. The figures, therefore, should not be interpreted as accurately reflecting the relative sizing or positioning of the corresponding structural elements, the magnitude or value of any parameter or the composition of any particular composition or compound according to the example embodiments of the invention.

DETAILED DESCRIPTION OF EXAMPLE EMBODIMENTS

Figure 1:
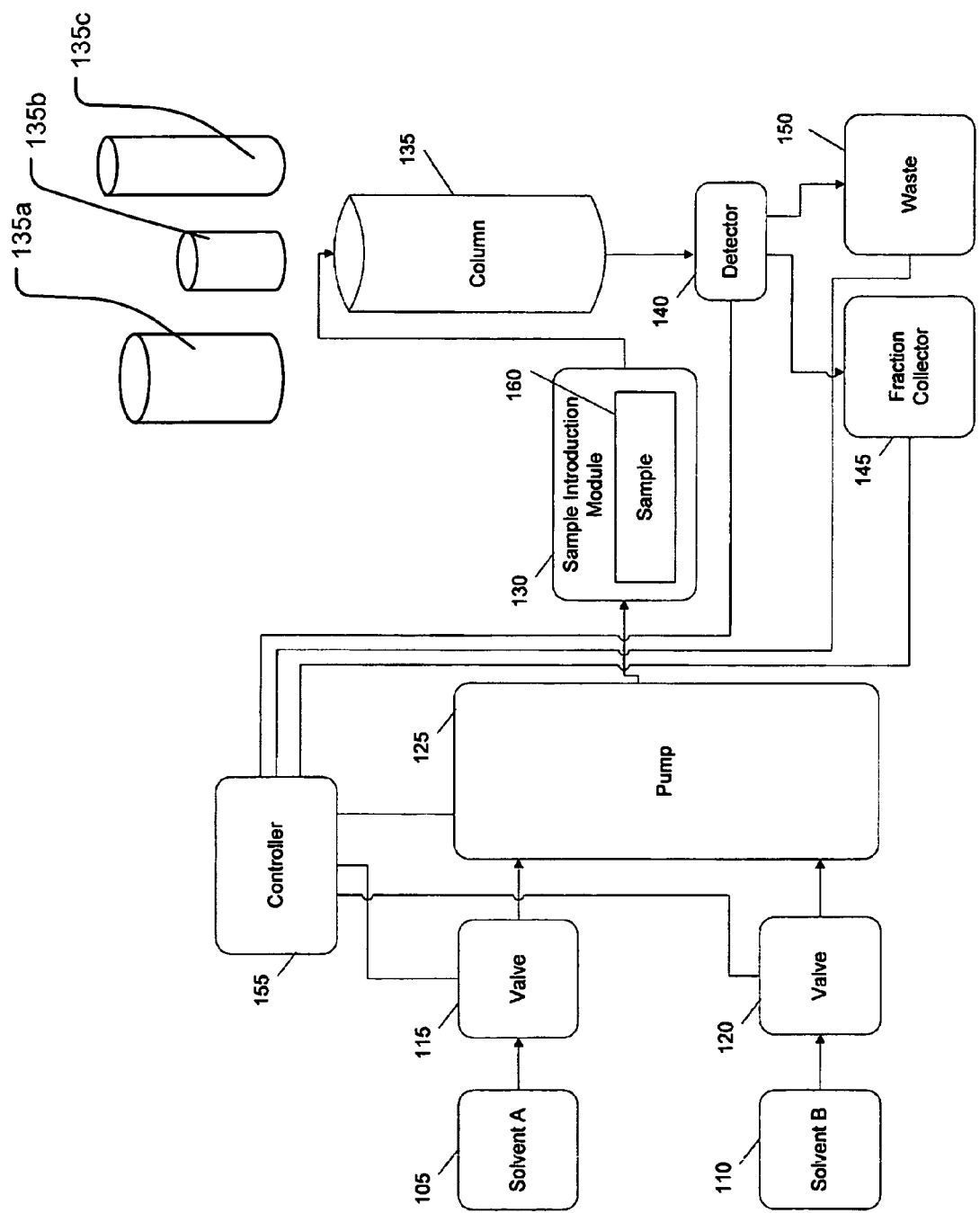
FIG. 1 is a block diagram of a column chromatography system that may be utilized in performing the methods according to the example embodiments of the invention.

FIG. 1 is a block diagram of a column chromatography system according to an example embodiment of the invention. As illustrated in FIG. 1, the chromatography system includes solvent sources 105 and 110, valves 115 and 120, a pump 125, a sample introduction module (SIM) 130, a column 135 (which may be selected from a group of available columns 135a, 135b, 135c), a detector 140, a fraction collector vessel 145, a waste collector vessel 150, and a controller 155. Chromatography is performed in the system of FIG. 1 by preparing the chromatography system for use and providing the necessary inputs to the controller 155. Preparing the system for use may include, for example, loading a first solvent A and a second solvent B in the solvent sources 105 and 110, respectively, and loading a sample 160 into the SIM 130.

Inputs provided to the controller 155 may include, for example, commands corresponding to specific tasks be performed, for example, a command requesting the pump 125 to operate at a certain flow rate for a certain period of time, or may comprise a more general request that will initiate a series of specific tasks are performed, for example, requesting that the system perform chromatography on a sample over a linear gradient profile, as will be discussed in greater detail in reference to FIG. 4. As suggested above, other inputs may typically include TLC retention factor ($R_f$) information for two or more of the compounds present in the sample and information regarding the composition of the solvent system used for obtaining the retention factor information. Other possible inputs include, for example, certain values such as temperatures, flow rates, primary detector wavelength, secondary detector wavelength, sample vessel size, cartridge size, sample load size, equilibration duration, and/or collection receptacle pattern(s) that the chromatography system may use in performing chromatography. Yet other inputs may include, for example, explicit values or ranges for parameters and/or conditions to be utilized by the controller 155 in performing the separation and/or the collection, format and/or output of data collected or generated during the separation.

In general, the chromatography system operates by having the controller 155 cause the valves 115 and 120 to open to various degrees, thereby adjusting the delivery of solvent from each of the solvent sources 105 and 110, respectively, and controlling both the total solvent flow rate and the ratio of the solvents. For example, if the valves 115 and 120 are positioned to allow the volume of solvent A entering the system to be twice that of the volume of solvent B entering the system a 2:1 ratio of solvent A to solvent B can be obtained.

The solvents are pumped through the valves 115 and 120 to the SIM 130 by the pump 125 which may also control the flow rate of the solvents into the SIM and then through the attached column 135. Upon entering the SIM 130, the solvents flow around, through, or over the sample 160 that resides in the SIM 130 and thereby begin dissolving components of the sample 160 and be carried into the column 135. Although a SIM is used in the example embodiment of a chromatography system according to the invention, as will be appreciated by those skilled in the art alternative methods, mechanisms and/or techniques may be used instead of, or in addition to, a SIM for introducing the sample 160 into the chromatography system. Such methods, mechanisms and/or techniques may include, for example, liquid injection, solid injection, use of a sample dispensing module (e.g., a Biotage AB Samplet™ cartridge), pre-absorption of a sample, or any other conventional approach effective for introducing a sample into a chromatography column.

Once at the column 135, the solvents and/or components of the sample 160 may pass from through the column 135 from an entry or introduction region at a first or upstream end to an exit or removal region at the opposite or downstream end. The solvents and the dissolved compounds from the sample 160 will pass through the column 135 at varying rates with the dissolved compounds exiting the column 135 at different times and in different volumes of the solvent. Solvents typically pass through the column 135 at a quicker rate than any of the dissolved components from sample 160. For example, if a mixture of solvents A and B are passing through the column 135 and carrying a dissolved component C from the sample 160, the component C will exit the column behind a certain volume of the solvent system. Column 135 may include a variety of materials that comprise a "stationary phase" (i.e., substance through which solvents and/or components of a sample pass). For example, the column 135 may include one or more stationary phases selected from a group including, for example, liquid-liquid, liquid-solid (adsorption), size exclusion, normal-phase, reversed-phase, ion exchange and/or affinity materials. The particular configuration of the chromatographic system is not limited and may include various numbers and/or combination of types of columns. In addition to the column 135, the chromatography system may include one or more additional types of column such as, for example, a guard, derivatizing, capillary, fast, scavenging, and/or preparatory column.

The detector 140 detects the various liquids and/or compounds that exit the column 135. The detector 140 may be any type of detector and may utilize any conventional technique for detecting substances that exit the column 135. For example, the detector 140 may include one or more of refractive index, ultra-violet, fluorescent, radiochemical, electrochemical, infrared, near-infrared, mass spectroscopy, nuclear magnetic resonance and light scattering detectors. The detector 140 is typically selected to provide a sufficient sensitivity for differentiating between the components of solvent system (background) and the various compounds exiting the column 135. The detector 140 also typically generates corresponding signals that may be interpreted, analyzed and/or monitored by the controller 155 for selectively controlling the flow of certain liquids and/or compounds containing in portions of such liquids into the fraction collector apparatus 145 while directing unwanted substances into a waste collector vessel 150.

The controller 155 may be any type of computer system and may control any number of aspects and/or components of the chromatography system. For example, the controller 155 may be a computer system including a data processor and operator interface; the controller 155 may include only a data processor and the controller 155 may interface with another computer system for operator input and/or output; or any combination of the two. As an example of a controller that interfaces with another computer system, the controller 155 may automate control of the chromatography system and the controller 155 may interface with a personal computer. With such a configuration, an operator may use the personal computer to input commands and/or program the controller 155. In addition, the personal computer may receive output from the controller 155, such as chromatography results representing the results of chromatography performed on a sample. Output from the controller 155 may be further manipulated on the personal computer and/or displayed on a display device associated with the personal computer.

Although FIG. 1 depicts only two solvent sources (i.e., 105 and 110), in alternative implementations any number of sources may exist and those sources may be selectively chosen by the controller 155. For example, four sources may exist, each of which is associated with a corresponding valve, and the controller 155 may chose two or more of the sources from which solvents may be pumped through the chromatography system and the relative flow rates of the selected solvents to achieve the desired gradient profile. In addition, as appreciated by those skilled in the art, various of the other features of the example embodiment of a chromatography system according to the invention as illustrated in FIG. 1 may vary. For example, the system need not include the fraction collector vessel 145 and waste collector vessel 150. According to another example embodiment, the chromatography system may include more than one pump and may, for example, include both high volume and low volume pumps in order to improve control of the flow rates and solvent composition ratios across a wide range of volumes and compositions. For example, each of the solvent sources 105 and 110 may be associated with at least one dedicated pump. Similarly, the chromatography system may include any number of lines, valves and/or pumps that may be coordinated by the controller to achieve the desired solvent flows and compositions. For example, the chromatography system may not include any detector.

Figure 2:
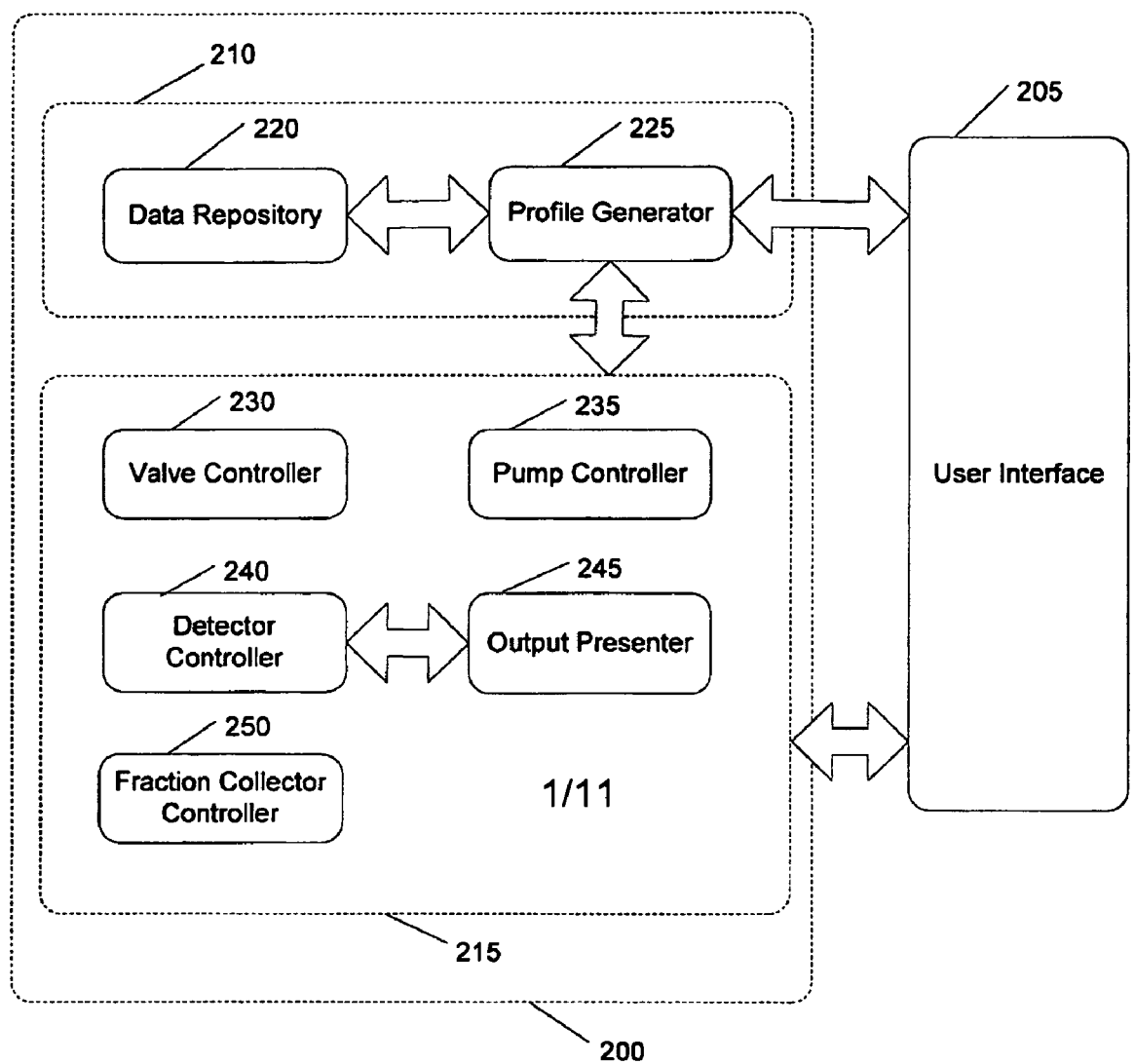
FIG. 2 is a block diagram of a chromatography controller of a chromatography system capable of performing the methods according to the example embodiments of the invention.

FIG. 2 is a block diagram of a chromatography controller 200 according to an example embodiment of a chromatography system according to the invention. The arrows in FIG. 2 represent dataflow among the various components of the chromatography controller 200 and/or between the chromatography controller 200 and the operator interface 205. As illustrated in FIG. 2, the chromatography controller 200 includes a profile generation system 210 and a main controller 215 that may be configured to interact with the operator interface 205. The operator interface 205, which may be embedded in a chromatography system or interface with a chromatography system, includes at least one input device for receiving an input from an operator and at least one output device for presenting output to an operator. For example, the operator interface 205 may be configured as a touch screen device or a combination of a keyboard and a display device. The operator interface 205 may exhibit any type of graphical interface, such as a graphical operator interface or a command-line interface. Operator input may include commands and/or data for performing chromatography in a chromatography system, such as the chromatography system of FIG. 1, and input may be received at the profile generation system 210 or the main controller 215.

The profile generation system 210 generates gradient profiles that indicate conditions for performing the desired chromatography/separation. The profile generation system 210 includes a data repository 220 and a profile generator 225. The profile generator 225 may be configured to generate, for example, linear gradient, step, or non-linear gradient profiles that include conditions for performing chromatography in response to various combinations of input. In general, a profile generated by the profile generator 225 includes a starting point and an ending point, connected by a line, where the starting point represents a starting ratio of two solvents and the ending point represents an ending ratio of the two solvents. For example, an operator may input data indicating $R_f$ values for at least two compounds, a solvent ratio corresponding to the TLC configuration used to generate the $R_f$ value, and data indicating the solvents present in the TLC solvent system. In response to the various inputs, the profile generator 225 may automatically generate gradient profile, for example a linear gradient profile, for use in the column chromatography system of which the controller 200 is a part.

That gradient profile will include a starting ratio and an ending ratio for the solvents comprising the solvent system. Based on the starting and ending ratios and addition input or configuration, the profile generator 225 may generate intermediate ratios between the initial and final ratios that provide for a linear, non-linear or stepped progression between the starting and ending ratios, respectively. Additional conditions for performing chromatography in a column chromatography system may also be generated. For example, the chromatography conditions may encompass parameters including, for example, column size, sample mass, sample load, separation duration (e.g., column volume of the solvents) and/or other parameters and conditions.

Figure 3:
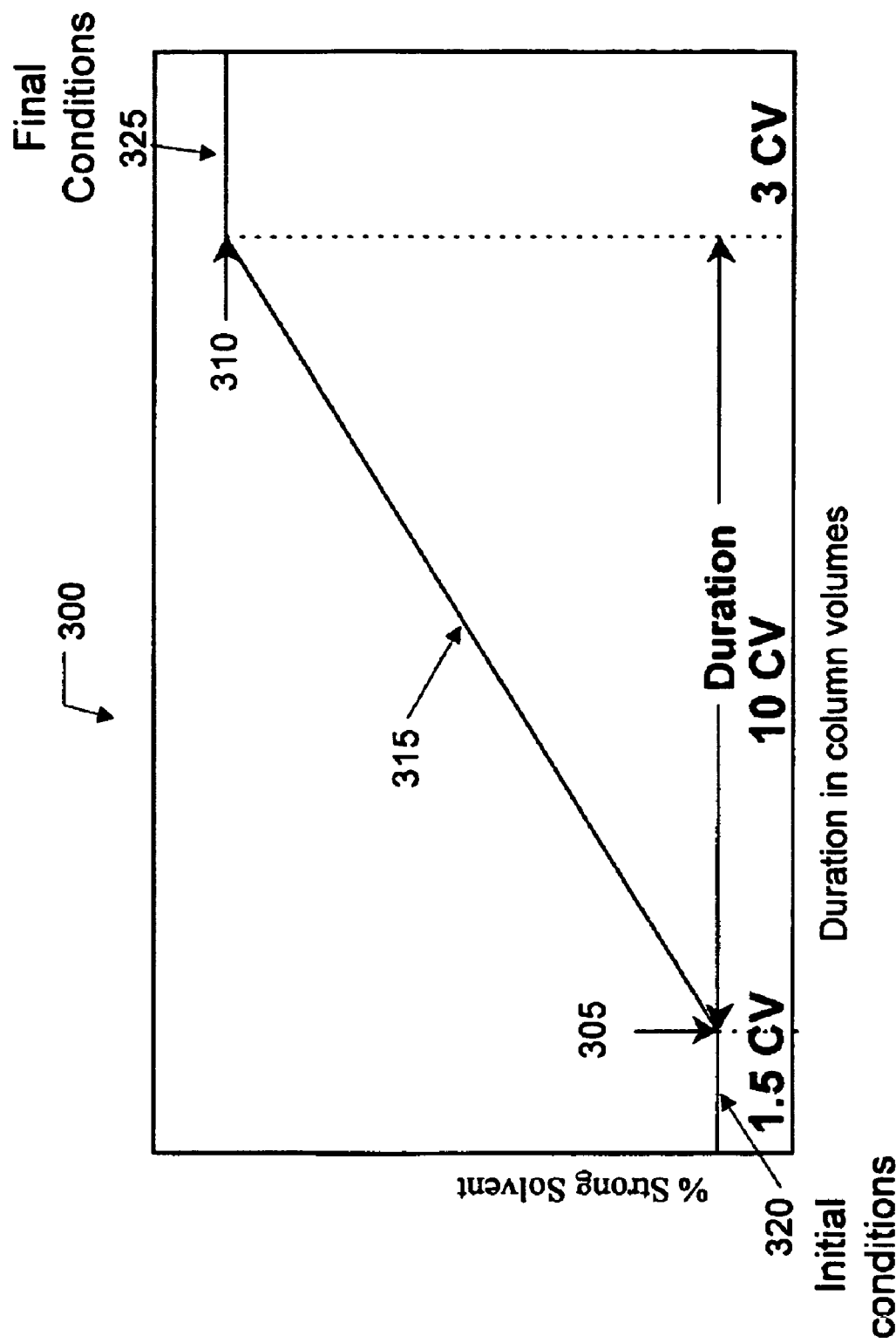
FIG. 3 is an example linear gradient profile that may be generated by chromatography controllers according to example embodiments of the invention.

FIG. 3 illustrates an example of a linear gradient profile 300 that may be generated by a profile generator such as the profile generator 225. The linear gradient profile 300 includes a starting point 305 and an ending point 310, connected by a substantially linear portion 315. The profile 300 indicates conditions for performing chromatography in a column chromatography system. The starting point 305 represents a starting ratio of two solvents at which a linear trend starts and the ending point 310 represents an ending ratio of the two solvents at which the linear trend ends. The horizontal axis represents duration and expresses the amount of solvent that should be pumped through a chromatography system over time. The horizontal axis of profile 300 is expressed in units of column volume, time or volume (i.e., the number of column volumes required, amount of time required, or the volume of solvent required for a particular purification.). The left vertical axis represents the ratio of the two solvents and is expressed as a percentage of the amount of the stronger solvent over the total amount of the solvents. Thus, any point in the graph represents a solvent ratio that should be pumped in the chromatography system after a certain amount of total solvents has been pumped into a chromatography system. The profile 300 has a positive trend that indicates that the solvent ratio increases over the substantially linear portion 315 (i.e., the solvent strength increases over the substantially linear portion). Other profiles generated by the profile generator may have a negative trend indicating that the solvent ratio is decreasing, or any combination of trends indicated by any of a number of gradient portions. For example, a linear gradient profile for three solvents R, S, and T may include a first gradient portion indicating an increasing ratio of R compared to S. Then, a second gradient portion may be connected to the first gradient portion and the second gradient portion may indicate a decreasing amount of R compared to the solvent T.

In addition to the gradient portion 315, the profile 300 includes linear portions 320 and 325 (i.e., step portions). The linear portion 320 represents an amount of solvent that is pumped through the chromatography system as an initial solvent conditioning process for the column and may represent the starting separation conditions from which the solvent ratio will be increased after the starting point 305. The linear portion 325 represents a final solvent condition or composition during which a volume of the solvent pumped through the system after the gradient ending point 310. The duration of each of the portions 315, 320, and 325 maybe determined based on predefined amounts, calculated based on column information (e.g., the gradient portion 315 should be calculated based on the size of the column to be used), or some combination thereof. In FIG. 3 the durations of the portions 320, 315, and 325 are calculated based on a column size, hence the durations 1.5 CV (column volumes), 10 CV, and 3 CV, respectively.

As discussed above, a solvent ratio may be represented as the amount of a stronger solvent, in a two solvent system, over a total amount of the two solvents. A solvent may be classified as relatively weaker or stronger than another solvent based on the relative solvent strength (e.g., the polarity) of the respective solvents. Referring back to FIG. 2, relative solvent strength values of the solvents may be indicated as input to the controller 200 or may be determined based on the input. For example, if two solvents are indicated as hexane and methylene chloride ($MeCl_2$), the profile generator 225 may determine, based on the reference of a table of polarities of various solvents, that methylene chloride is a stronger solvent. Thus, a solvent ratio based on these two solvents may represent that volume of methylene chloride over the total volume of the two solvents. For example, if there were five parts hexane in a composition with one part methylene chloride (i.e., 5:1), the ratio may be expressed as 1/6 (i.e., 1 part methylene chloride over 1 part methylene chloride and five parts hexane).

Profiles generated by the profile generator 225 need not be expressed by the same metrics or units as the example profile 300 of FIG. 3. For example, the horizontal axis may be expressed by other types of metrics, such as time (if so, time may be converted from other data using the equation: time=n*CV/F, where n is a variable that may represent a number of columns, CV is a column volume, and F is a flow rate). Also, the horizontal axis may be expressed by other units and these units may depend on the metrics that define the axis. For example, the horizontal axis may be expressed in units such as milliliters if the axis is defined in terms of volume. As another example, the vertical axis may be expressed in another form than the percentage of the strong solvent, to express a change in the solvent composition. In addition, the trend of a linear gradient profile may vary. For example, the incline may be less steep. Also, linear gradient profiles generated by the profile generator 225 may be expressed in different formats. For example, a profile may be represented as a gradient table and that table may include a starting point, an ending point, and different values corresponding to different durations within the profile. In addition, the table may include other conditions suggested for performing chromatography, such as a range of columns that are suggested for use with the profile.

The data repository 220 will typically include various types of data that may be referenced for generating profiles. As will be appreciated by those skilled in the art, the data repository 220 need not necessarily be present in the primary chromatography apparatus so long as it remains accessible to the controller, for example, on a remote server, whereby it may be accessed by the controllers from multiple chromatography systems. This data may be organized in or distributed throughout one or more databases or memory devices. For example, the data repository 220 may include a solvent strength database in which data relating to the relative solvent strength values of elutropic series (e.g., a relative ranking of solvents ranging from non-polar to highly polar), which may be referenced to determine the relative strength of solvents; a column database to store different attributes, such as volume, diameter, length and/or packing material, of a series of columns suitable for use in combination with the chromatography system; and, one or more additional databases for storing data that may include, for example, suggested maximum sample sizes, indexed by $R_f$ data and one or more column attributes (e.g., column diameter or make and model of a column, and a difference in column volumes), one or more general algorithms and/or algorithms more precisely tailored to particular combinations of solvents, materials, columns, and/or sub-ranges of the solvent systems that can be accommodated by the chromatography system.

The main controller 215 includes a valve controller 230, a pump controller 235, a detector controller 240, an output presenter 245, and a fraction collector controller 250, each of which is typically configured to control various aspects of a chromatography system. The main controller 215, for example, may control the overall operation of a chromatography system as it performs chromatographic separations in accordance with the conditions included in a linear gradient profile, such as the example linear gradient profile 300. A linear gradient profile may be supplied to the main controller 215 by the profile generator 225. In addition, the main controller 215 may be configured to solicit, acknowledge and/or response to one or more inputs received via the operator interface 205 or other input or memory device.

The valve controller 230 controls the throughput of solvents through any number of valves in a chromatography system by controlling the degree to which valves may be opened. The pump controller 235 controls the operation of any number of pumps in a chromatography system by controlling whether the pumps are supposed to be operating and the flow rate at which the pumps should operate. As will be appreciated by those skilled in the art, an alternative configuration of the solvent delivery system may incorporate pressurized solvent sources 105, 110 and thereby avoid the need for downstream pumps and utilized "upstream" pumps to maintain a desired pressure range within the solvent sources. Thus, the flow rate and solvent composition may be controlled by the pump controller 235 and the composition by the valve controller 220. The detector controller 240 receives data that indicates substances passing through a detector flow cell from a detector, such as the detector 140 of FIG. 1, and may send data to the output presenter 245. The output presenter 245 presents data to the operator interface 205, such as, for example, data representing sensed substances in a chromatography system or other data related to performing chromatography. In addition, the output presenter may present other data, such as the status of a chromatography system. The fraction collector controller 250 receives data from the detector controller 240 and may control whether substances are directed to a fraction collector vessel or a waste collector vessel.

Although the components of the chromatography controller 200 are organized as the profile generation system 210 and the main controller 215, the components may be organized differently. For example, the components of the profile generation system need not be separate from the main system and might be a single system. Also, the chromatography controller 200 may include different and/or additional components. For example, the controller 200 may interface with a computer system that may send and receive data from the controller 200. In alternative implementations, the chromatography system may have additional and/or different data flow than is depicted in FIG. 2.

Figure 4:
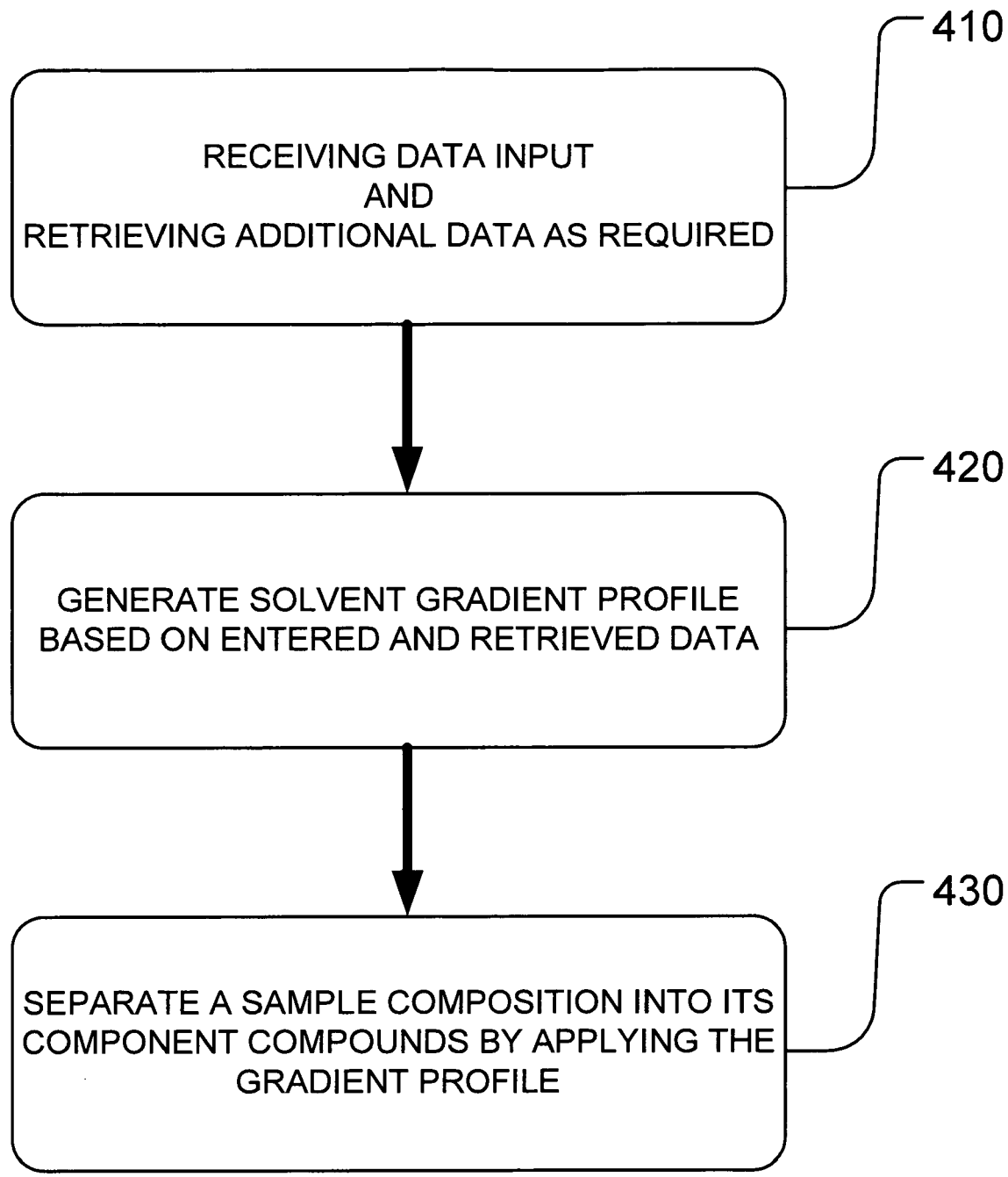
FIG. 4 is a flowchart of a method of performing chromatography according to an example embodiment of the invention.

FIG. 4 is a flowchart of a method of performing chromatography. The method depicted in FIG. 4 is performed by a chromatography controller, such as the chromatography controller 200 described in reference to FIG. 2. At 410 input is received by the chromatography controller. The input includes data that may be used by the chromatography controller to calculate conditions for performing chromatography with two or more solvents over a linear gradient profile. The input may include information that would correspond to performing TLC on a sample composition using combinations of two solvents. Thus, the input may be used to adjust conditions and transfer separation conditions from TLC to column chromatography.

As an example, the input may include an indication of two or more retention factors ($R_f$) corresponding to different compounds from the sample composition, an indication of a solvent ratio that produced the reported $R_f$ values, and an indication of the solvents present in the solvent system and their ratio. An indication of an $R_f$ value may be an $R_f$ value or one or more values that may be used to calculate an $R_f$ value. For example, an $R_f$ value of 0.2 may be inputted, or the $R_f$ value may be indicated by a distance of a component of a sample composition traveling up a TLC plate and the distance a solvent traveled up the TLC plate (e.g., 2 millimeters and 10 millimeters, respectively).

Continuing with the example input, the input may indicate a solvent ratio. The solvent ratio corresponds to the TLC conditions and indicates the ratio of the two solvents that may have been used to perform TLC separation on the sample composition. The solvent ratio may be expressed in any of a number of formats, such as a percentage of a stronger solvent of two solvents. For example, if two solvents corresponding to an $R_f$ value were a solvent A and a solvent B and the $R_f$ value corresponded to one part solvent A and four parts solvent B, where solvent A had a stronger relative solvent strength among the two solvents, the solvent ratio may be expressed as 20% (i.e., 100×solvent A/(solvent A+solvent B)=100×(1/(1+4))).

Continuing with the example input, the input may indicate two solvents. This information may be used to determine the relative strength of the two solvents (i.e., which of the two solvents is weaker or stronger, among the two solvents). As one example, the input may indicate that a first solvent is stronger than a second solvent. As another example, the input may indicate the type of the solvents and based on that input the controller may determine which of the two solvents is stronger or weaker. This determination may be made by reference to a table of solvent strengths that may be stored in a solvent strength database. For example, in a chromatography system for normal-phase chromatography, a table may store polarity values and using the polarity values the controller may determine a strong solvent. In reversed-phase chromatography this determination may differ because the relative solvent strength may be defined differently, thus the determination of a strong solvent may differ.

In addition to input related to performing TLC on a sample composition, the input may include other information that may be useful for generating conditions for performing column chromatography over a linear gradient profile. For example, the input may indicate a column to be used in the performance of column chromatography. Column input may include the dimensions of the column or information related to a make and/or model of a column. If the make and/or model of the column is included as input, the controller may determine the dimensions (e.g., volume, diameter, and length) of the column from a database of column information. As will be discussed later, column choice information may be used to determine the duration of a gradient profile and/or the flow rate to be used when performing column chromatography.

Based on the input of 410, a linear gradient profile is generated at 420. The linear gradient profile may be generated without further operator input, which may facilitate an automatic transfer of separation conditions to column chromatography from the TLC data input at 410. The linear gradient profile includes the conditions for performing column chromatography over that profile. For example, the linear gradient profile may include an initial conditions portion, a gradient portion, and final conditions portion. In that profile, the initial and final conditions portions have no incline and are defined by the starting and ending points, respectively, and, the gradient portion has an incline that is defined by the starting and ending points. Each point along the profile may indicate a ratio of the solvents that should be used to perform chromatography. Any technique may be used to generate a linear gradient profile, such as the technique discussed in reference to FIG. 5 and any of a number of conditions may be generated for use in performing column chromatography.

At 430 a sample is separated using the linear gradient profile generated at 420 by performing column chromatography. The sample may be separated automatically or an operator may be prompted for input before performing chromatography. For example, a linear gradient profile may be generated and based on that profile a chromatography system may start performing column chromatography without further operator input. As another example, an operator may be asked if they wish to modify the profile and the operator may modify the profile before causing column chromatography to be performed. If an operator is enabled to modify a profile, any of a number of mechanisms and/or techniques may be used to modify the profile. When the controller presents the linear gradient profile as a series of data values, such as starting ratio, ending ratio, and duration, the operator may modify the linear gradient profile by changing these values or adding additional values to the series of data values. Changes to the linear gradient profile and other conditions for performing column chromatography may occur at any time before, during, or after a separation. For example, after a chromatographic run, an operator may decide to change the linear gradient profile or other conditions to optimize the conditions for performing chromatography in a subsequent chromatographic run.

Figure 5:
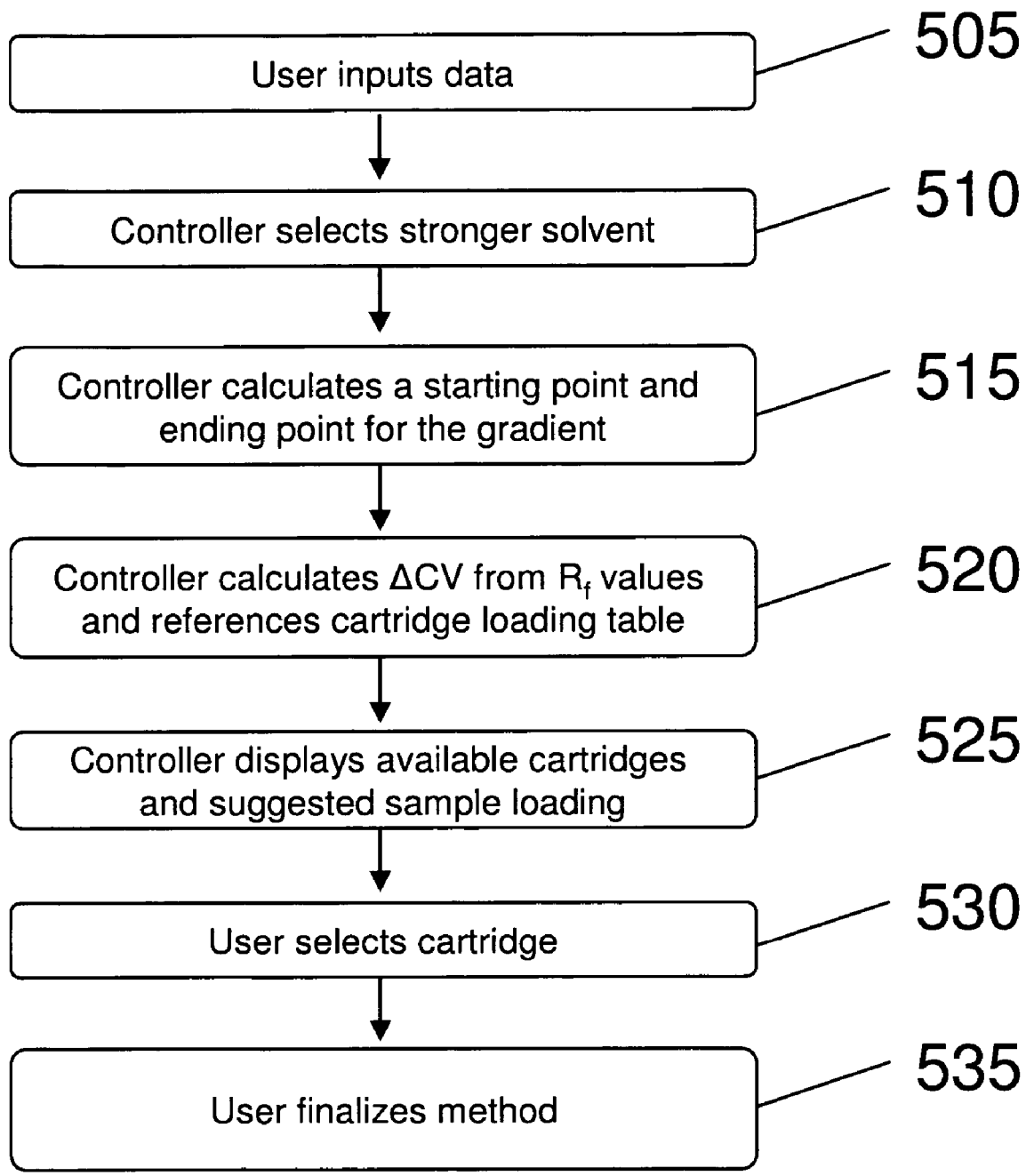
FIG. 5 is a flowchart of a method of generating a linear gradient profile according to an example embodiment of the invention.

FIG. 5 is a flowchart of a method of generating a linear gradient profile. The processes of FIG. 5 are performed by a profile generator, such as the profile generator 225 of FIG. 2. At 505 input is received at the profile generator. The input includes TLC data and may include a column designation or information regarding the range of columns available for use in the separation. TLC data corresponds to data generated during a TLC chromatographic run on a sample composition using a known solvent system, typically a binary solvent system wherein the two solvents are completely miscible. The TLC data includes an $R_f$ value, an identification of the solvents, and the composition of the TLC solvent system, i.e., the volume ratio of the component solvents.

Using TLC data for the key compounds, typically one compound of interest and the most closely adjacent (e.g., the compound on the TLC plate that will generate the smallest $\Delta R_f$ (and/or the smallest $\Delta CV$) relative to the compound of interest) or the most closely adjacent compounds having both a higher and a lower $R_f$ than the compound of interest, and the solvent system, the control system may select from one or more algorithms for predicting operating conditions suitable for separating the compound of interest from the adjacent compound(s) for a range of solvent systems. As will be appreciated by those skilled in the art, the algorithm and the system programming may be adapted to compensate and/or adjust for the particular solvent system, the available columns and the $\Delta CV$ projected from the TLC $R_f$ data. As will be appreciated, for example, methanol may be utilized in solvent mixtures particularly useful for separating highly polar compounds and/or basic compounds.

An exemplary binary gradient method may be defined with starting B1 and ending B2 concentrations of a solvent B with the concentration increasing from B1 to B2 over a ten (10) column volume (CV) period. This approach has proven adequate for eluting many target compounds.

A compound's TLC retention is characterized with a retention factor parameter $R_f$ that corresponds to a ratio between the distance the compound has moved from the origin (b) compared to the distance the solvent (a) has moved from the origin measured at the solvent front. The more polar solvent (B0) component in a TLC solvent mixture tends to exhibit a strong relationship to the measured $R_f$ values for a range of organic compounds with the $R_f$ value increasing and the CV value decreasing ($CV=1/R_f$) with increasing percentages of the polar solvent. % B0 is the percentage of solvent B used in the TLC system used to generate the $R_f$ data.

For example, in a 3:1 hexane/ethyl acetate TLC system, where ethyl acetate is B, the value of % B0 may be calculated according to equation (2):

$$\% B0=100\%*[B/(B+\text{Balance})] \qquad (2),$$

which, in this case provides a % B0 of 25%:

$$100\% * [1/(1+3)] = 25\%.$$

Transferring data obtained from a TLC analysis to a FLASH chromatography separation takes % B0 values obtained from the TLC analysis and derives the starting (B1) and ending (B2) conditions for the linear gradient method by applying the following equation (3) to calculate B1:

$$\% B1 = \% B0/4 \quad (3).$$

For example, a TLC system with 5:1 hexane/methylene chloride produces an $R_f = 0.2$ for a compound. Applying equation (2) to this data we obtain:

$$\% B0 = 100\% [1/(1+5)] = 16.7\%$$

and $$\% B1 = 16.7\%/(4) = 4\% \text{ (rounded to the nearest whole percent)}.$$

If % B1 is below 2%, the % B1 may simply be set to 0% for convenience. If the $R_f$ value is below 0.1, a more effective TLC solvent system should be identified that will produce a $R_f$ value of at least 0.1.

For a linear gradient separation, the ending condition % B2 may be calculated according to equation (4):

$$\% B2 = 2 * B0 \quad (4).$$

The column volume (CV) is then used to calculate gradient volumes. A conventional profile for column volumes in a linear gradient system starts with the initial % B1 solvent composition and maintains this solvent composition for some initial volume flow, typically at least 1.0 CV. The solvent ratio in the solvent composition is then ramped from the initial % B1 composition to the final % B2 solvent composition over an extended volume flow, for example, 10 CV. This final solvent composition is then maintained for an additional final volume flow, for example, 2 CV, to flush the column. As will be appreciated by those skilled in the art, although the noted flow periods are expected to provide acceptable system performance, the flow periods used for the initial, ramp and final portions of the gradient flow may be independently modified if desired.

In alternative implementations, other types of data may be received as input at 505. For example, rather than receiving $R_f$ values, the distances that components of a sample traveled up a TLC plate and the distance that a solvent front traveled up the TLC plate may be received as inputs from which the system may calculate the $R_f$ values. As another example, rather than receiving the identity of the two solvents, an identification of which solvent is stronger may be received. From that information, the processes of 515-535, or similar processes, may be performed. Also as another example, more than two solvents may be received as input and that input may be combined with other input that indicates two gradients should be generated for a gradient profile. And, as another example, more than two $R_f$ values may be received as inputs, where each $R_f$ value corresponds to a component in a sample composition. The additional $R_f$ value may be used to generate a $\Delta CV$ value from which conditions for performing chromatography may be generated, as will be discussed later.

At 510, a determination is made as to which of the two solvents is stronger (i.e., a strong solvent) if not previously input by the operator or retrieved from the data repository. This determination may typically include referring to a table or other data that provides relative solvent strength values (i.e., the relative strength of each solvent in the solvent system relative to any number of solvents) for solvents and, based on two relative solvent strength values, determining that one solvent is stronger. In alternative implementations, other techniques and/or mechanisms may be used to determine which solvent is stronger, and the techniques may vary depending on the type of chromatography desired to be performed. For example, the techniques may vary depending on whether normal-phase or reversed-phase chromatography is desired to be performed.

At 515, the controller creates a basic gradient profile containing an initial portion, a ramp portion and a final portion.

At 520, the controller calculates $\Delta CV$ from input $R_f$ values, which may be used to predict sample load.

At 525 the profile generator determines whether the input included a column choice (i.e., a selection of a column that will be used to perform column chromatography using the linear gradient profile). If the input included a column choice, the column dimensions are determined based on an access of a database including column data and the duration of portions of the linear gradient profile are generated based on the dimensions of the column. If variables are used to define the duration of portions of the linear gradient profile, values may be automatically assigned to those variables at a later time. For example, 10 column volumes may be defined as the duration of the gradient portion of the linear gradient profile. At a later time, when column chromatography is going to be performed, the column choice may be entered and the duration in terms of the actual volume of solvents that should be used may be calculated based on the dimensions of the chosen column.

In addition to the conditions indicated by the profile, as described above, other conditions may be generated by a chromatography system. For example, in one embodiment, the chromatography system may determine a target solvent flow rate based on column dimensions. The system may generate these conditions by referencing a database of suggested flow rates indexed by one or more column attributes (e.g., length and/or diameter and packing material). In another embodiment, the system may utilize conditions and parameters to determine a suggested maximum sample mass for performing column chromatography to improve separation of the target compound. For example, the chromatography system may generate a suggested sample mass based on two or more $R_f$ values and column attributes. The suggested sample mass may be generated by referencing a table of suggested sample masses indexed by column attributes and a $\Delta CV$ value (i.e., calculable from the two or more $R_f$ values). In other embodiments, the system may be configured to select from among a number of available columns and/or cartridges based on a target sample load size. In such systems, the controller may be configured to identify the column or cartridge that will provide at least a minimum degree of separation while limiting the amount of solvent required to achieve the separation. In other embodiments, the system may be associated with a selection and loading mechanism that may be configured for retrieving the designated cartridge and configuring and/or positioning the cartridge to receive both sample load and the solvent stream. Alternatively, the system may be associated with a distribution assembly through which the sample load and/or the solvent flow may be selectively directed to the designated column or cartridge.

In another embodiment, the system may provide a suggested column configuration or range of column configurations based on a projected sample mass and two or more $R_f$ values, by referencing a database of suggested column choices indexed by sample masses and $\Delta CV$ values. In such an embodiment, the solvent flow rate used when performing the column chromatography and the suggested starting and ending solvent ratios may be modified based on the attributes of a column chosen. For example, in order to provide the conditions as described above, at least two $R_f$ values are required to ensure that an acceptable $\Delta CV$ value can be obtained for the separation.

Although the examples discuss the use of a $\Delta CV$ value as a value that may be used to index suggested conditions for performing chromatography, other types of data may be used to index the suggested conditions. $\Delta CV$ represents a resolution value and may be easily adapted for any size column chosen for performing chromatography. The relationship between CV and $R_f$ may be expressed as $CV=1/R_f$; thus, two or more $R_f$ values may be used to calculate a $\Delta CV$ value by taking the inverse of two $R_f$ values and determining the difference of those CV values (i.e., $\Delta CV=CV_2-CV_1$ or $\Delta CV=(1/R_{f2})-(1/R_{f1})$). For example, for two $R_f$ values and 0.25, the corresponding CV values are 5.0 and 4.0, respectively, and a $\Delta CV$ value would be 1.0. The $\Delta CV$ value may be advantageous as the $\Delta CV$ may be a more reliable indicator for suggesting conditions for performing chromatography than $\Delta R_f$.

Although the processes of FIGS. 4 and 5 were described as being performed by a controller and a profile generator of a chromatography system, respectively, the processes may be performed by any of a number of components in a chromatography system and/or with components outside a chromatography system. For example, the processes included in 410 and 420 may be performed by a computer system that interfaces with a chromatography system and that chromatography system may perform the processes included in 430.

Also, although FIGS. 4 and 5 were described in relation to only two solvents, the same techniques described in reference to FIGS. 4 and 5 may be used for more than two solvents. For example, three solvents F, G, and E may be indicated as input to a chromatography system and an operator may indicate that they wish to have chromatography conditions generated that include a gradient profile with two gradient portions; a first gradient portion corresponding to solvents F and G, and a second gradient portion corresponding to solvents F and E. In that scenario, a gradient profile may be generated including the two gradients with the first gradient portion increasing the ratio of solvent F compared to solvent G and the second gradient portion increasing the ratio of solvent E compared to solvent F. In order to generate the gradient portions, the similar techniques as those described in FIGS. 4 and 5 may be used. For example, for each combination of two solvents that are relevant to the trend of increasing and/or decreasing solvent composition, an $R_f$ value may be used to define the gradient portion corresponding to those two solvents.

Although the method of FIGS. 4 and 5 are shown as being composed of a certain number and type of processes, additional and/or different processes may be used instead. Similarly, the processes need not be performed in the order depicted. For example, in FIG. 5, the processes of 525 may be performed before the processes of 520.

Figure 6A:
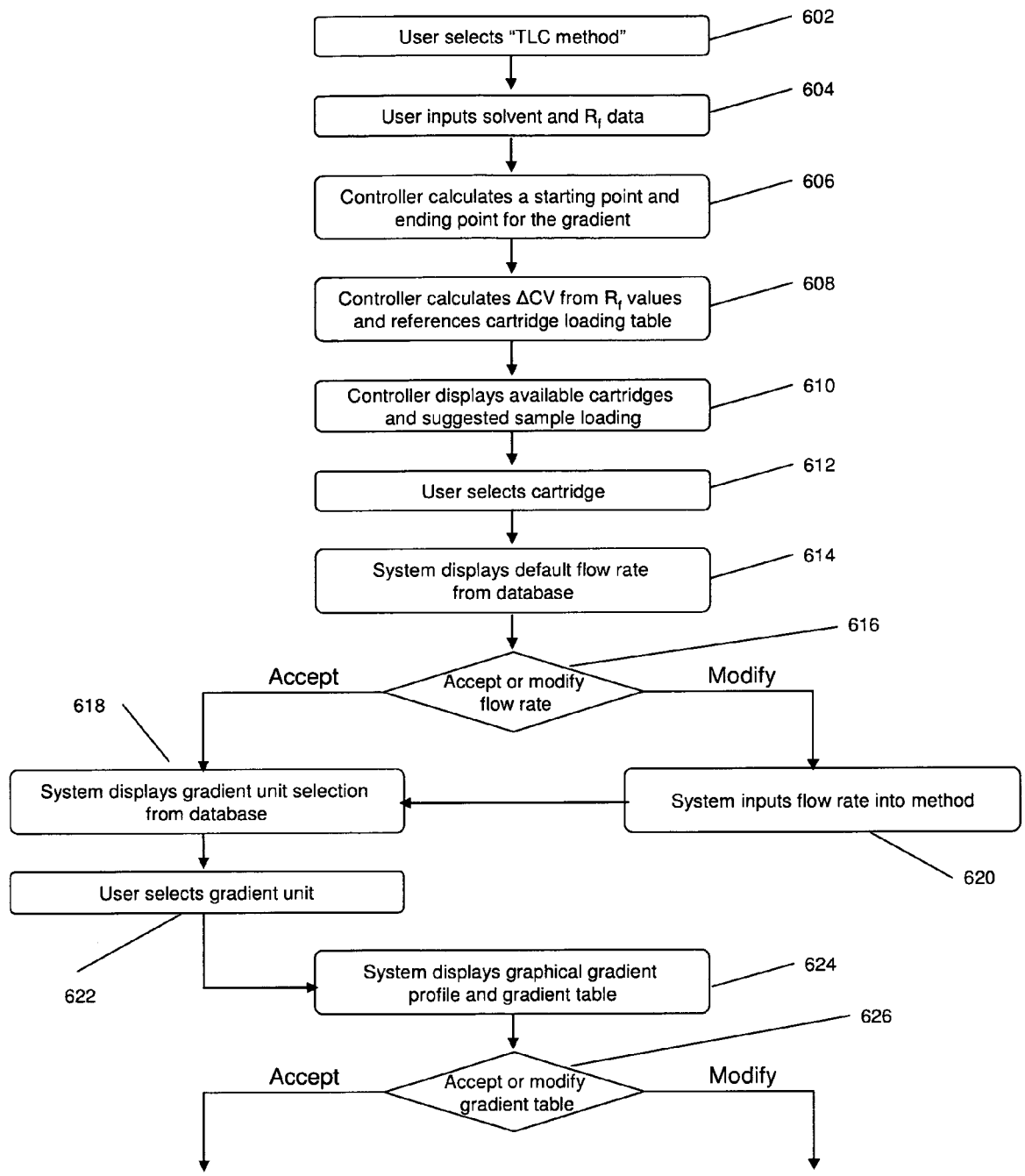
FIGS. 6A and 6B constitute a flowchart of a method of generating a linear gradient profile and separation method.
Figure 6B:
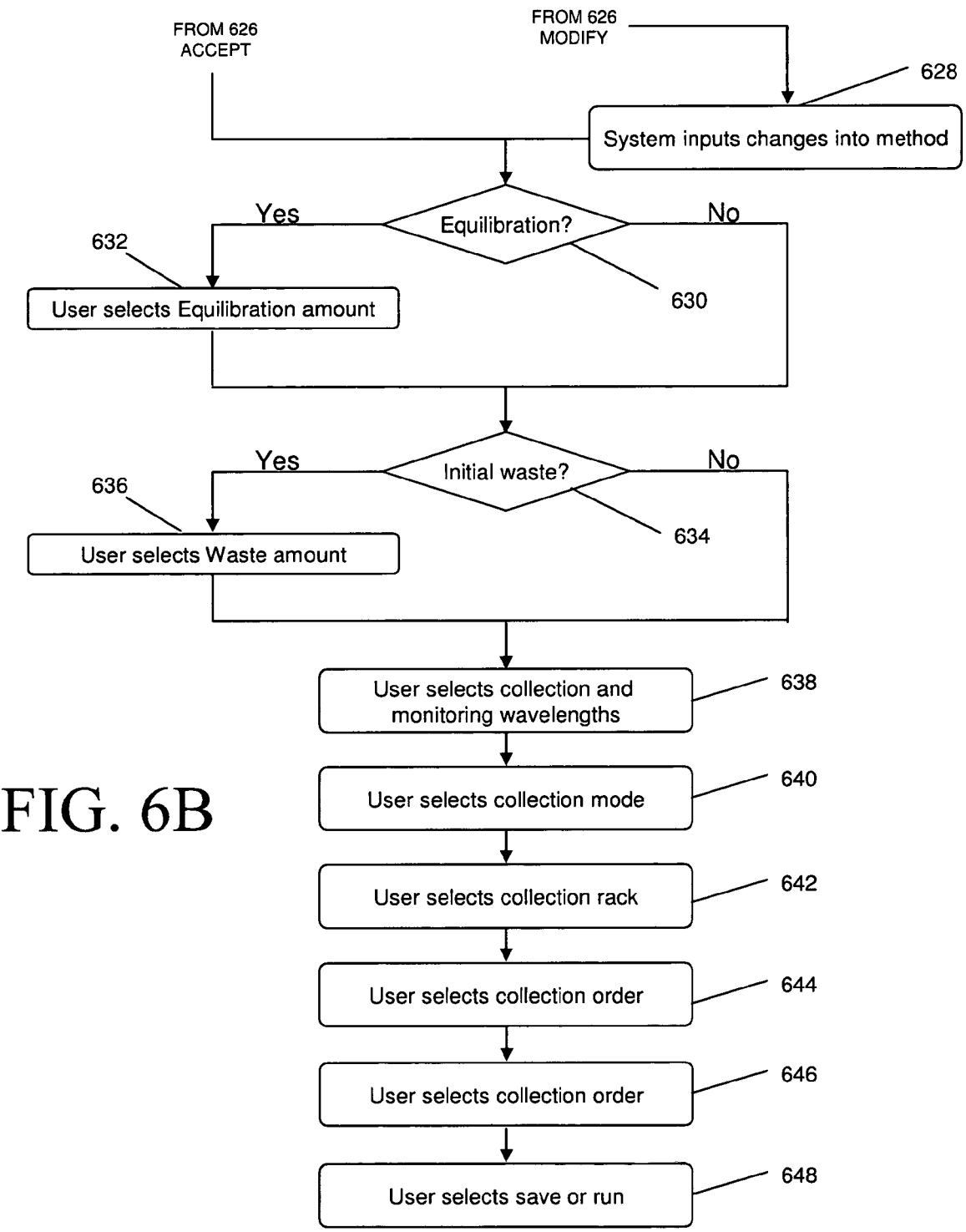

FIGS. 6A and 6B are a flowchart of a method of generating a linear gradient profile. The method implemented in FIGS. 6A and 6B may be a variation of the method illustrated in the flowchart of FIG. 5. Various inputs may be entered by an operator at 602 and 604 and/or received at 612. At 602, selects the TLC option from the menu. At 604, an operator enters TLC $R_f$ data, which includes at least two $R_f$ values (one for the compound of interest and one for an impurity) or data that may be used to calculate the relevant $R_f$ values, the solvents using either the name of the solvents or the type of solvents, and the amount of strong solvent.

In alternative implementations, if more than two $R_f$ values were input into the controller, multiple $\Delta CV$ values may be calculated, and a minimum $\Delta CV$ value may then be determined from a group of $\Delta CV$ values. The minimum $\Delta CV$ value may then be used as the representative $\Delta CV$ value for determining conditions sufficient to achieve the desired separation.

At 604, a determination is made as to which one of two solvents is stronger.

At 606, the system calculates the gradient start, ramp, and end points using the algorithms as defined in equations 3 and 4.

Figure 7:
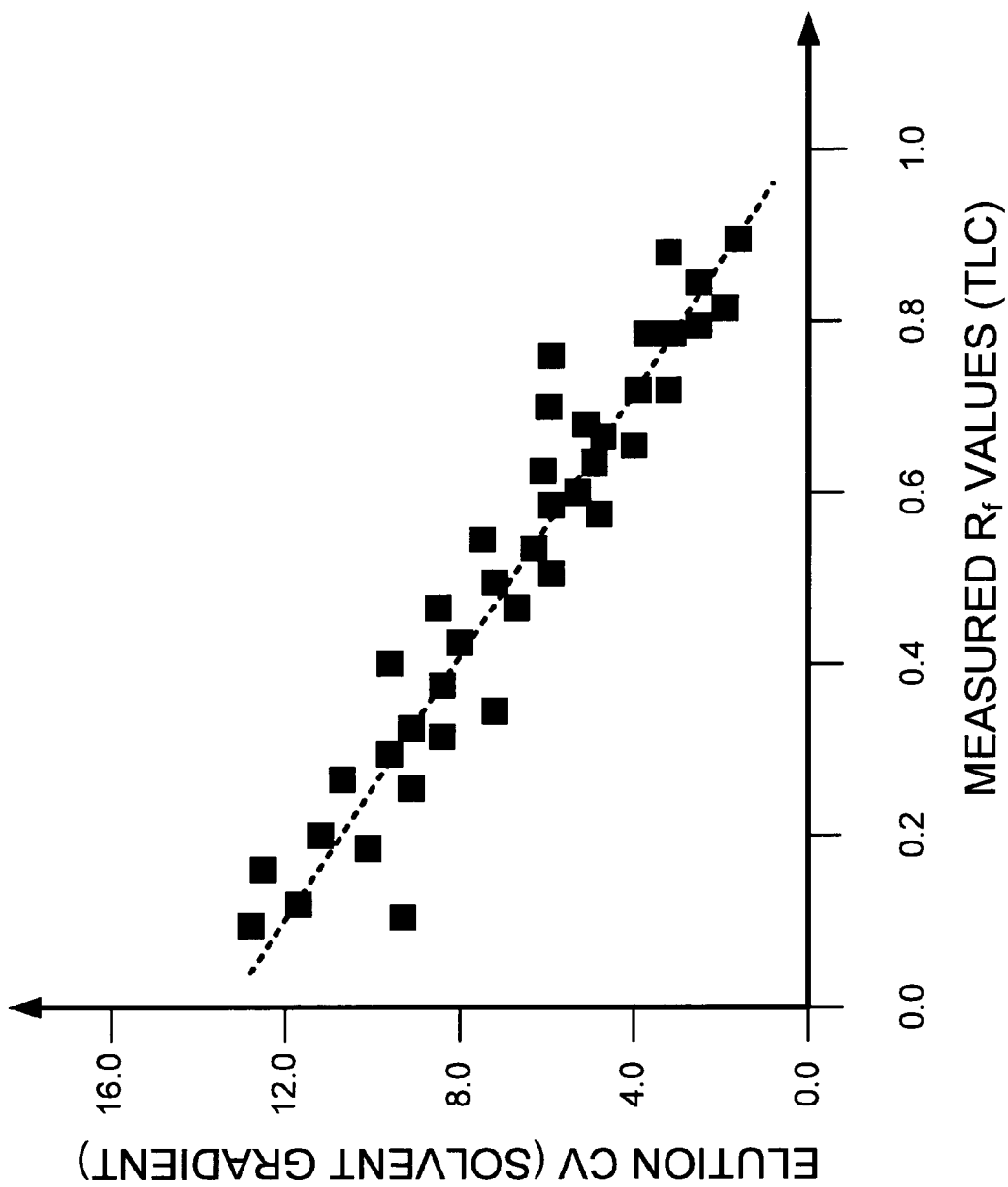
FIG. 7 is the relationship between $R_f$ and CV from a compilation of different linear gradients generated from experimental data that may be used in calculating ΔCV from $R_f$ values when practicing a method according to the example embodiments of the invention.

At 608, the controller calculates $\Delta CV$ and references the loading table that data for which is derived from equation I, and/or FIG. 7.

At 610, the available cartridge selection is displayed with an associated suggested sample load.

At 612, the user selects the appropriate cartridge.

At 614, the cartridge default flow rate is displayed.

At 616, the user either accepts the default flow rate or modifies the flow rate. If accepted, the gradient units offering is displayed 618, If modified 620, the system updates the method.

At 622, the user select the preferred gradient unit.

At 624, the gradient profile and gradient table are displayed.

At 626, the user accepts the gradient or modifies the gradient. If accepted, the user selects whether to pre-equilibrate the cartridge 630. If the gradient is modified 628, the system updates the method.

If equilibration is selected 630, the user enters an equilibration amount and duration. Once equilibration has been waived or accepted with the desired conditions, the user finishes the programming by selecting collection and monitoring wavelengths (if equipped with a multi-channel variable wavelength detector), collection rack and collection volume, and collection pattern 634–646.

Various implementations of the systems and techniques described here may be realized in digital electronic circuitry, integrated circuitry, specially designed ASICs (application specific integrated circuits), computer hardware, firmware, software, and/or combinations thereof. These various implementations may include one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known and referred to in the alternative as programs, software, software applications or code) may include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices) used to provide machine instructions and/or data to a programmable processor, including a machine-readable medium that receives machine instructions as a machine-readable signal. The term "machine-readable signal" refers to any signal used to provide machine instructions and/or data to a programmable processor.

In developing a flash separation procedure, several simple steps may be taken to produce an acceptable separation including:

1) Conducting TLC runs to identify a solvent system that produces a $R_f$ value of from 0.1 to 0.9, and preferably from 0.1 to 0.6, for the compound of interest;

2) Separating and purifying initial samples using a disposable column with or without a pre-column (to protect the main column);

3) Collecting fractions at least every 0.5 column volume or by detector-triggered collection signals; and 4) Analyzing the collected fractions using TLC, HPLC (high-performance liquid chromatography, and/or MS (mass spectroscopy) to determine if the target component is present and evaluate its purity.

Figure 11:
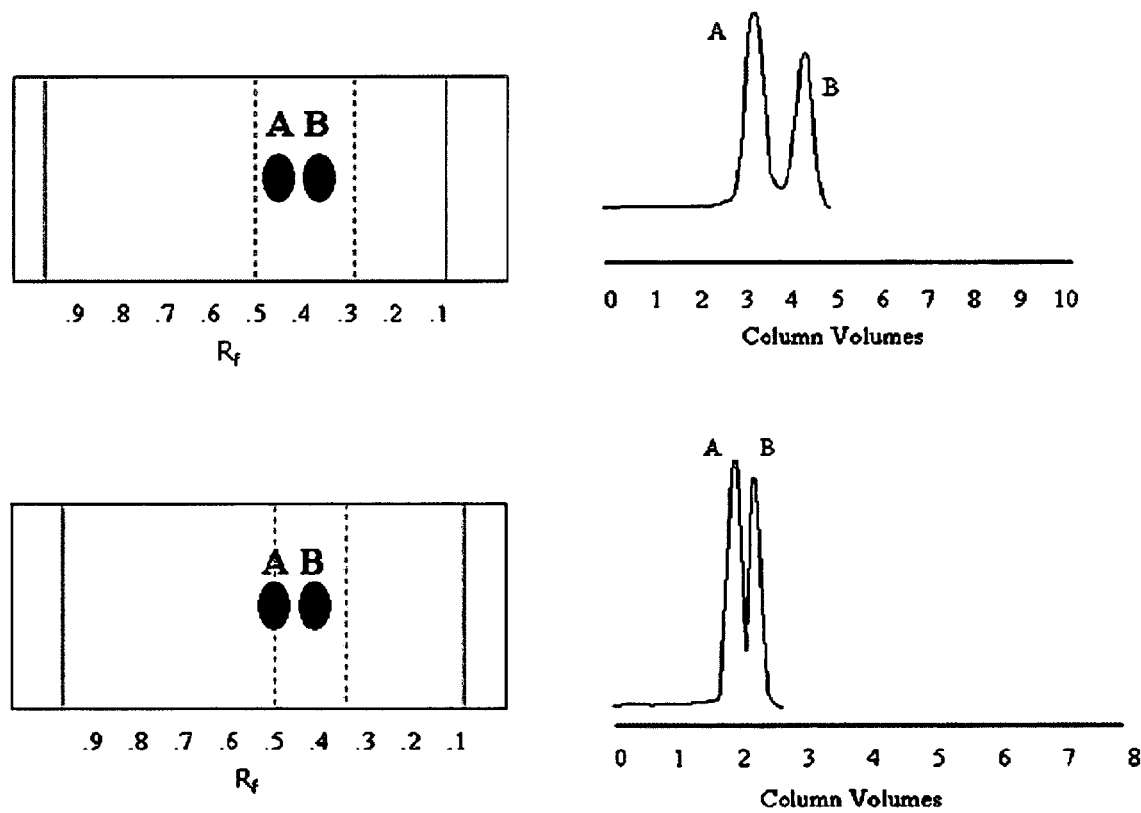
FIG. 11 illustrates the improved separations that can be achieved at lower $R_f$ values.

The first step is to obtain a TLC separation that exhibits both separation of the target component and an appropriate retention factor $R_f$ value. As illustrated in FIG. 11, improving the TLC separation, e.g., an increased $\Delta CV$ is achieved by reducing $R_f$.

Using a "slower" solvent system may greatly improve the degree of separation. As discussed above, TLC data may be used to predict column elution behavior using the relationship $CV=1/R_f$, where CV is the number of column volumes required to elute the component from the column regardless of column dimensions. In general, the better the separation, the better the sample load capacity of the column.

Figure 8:
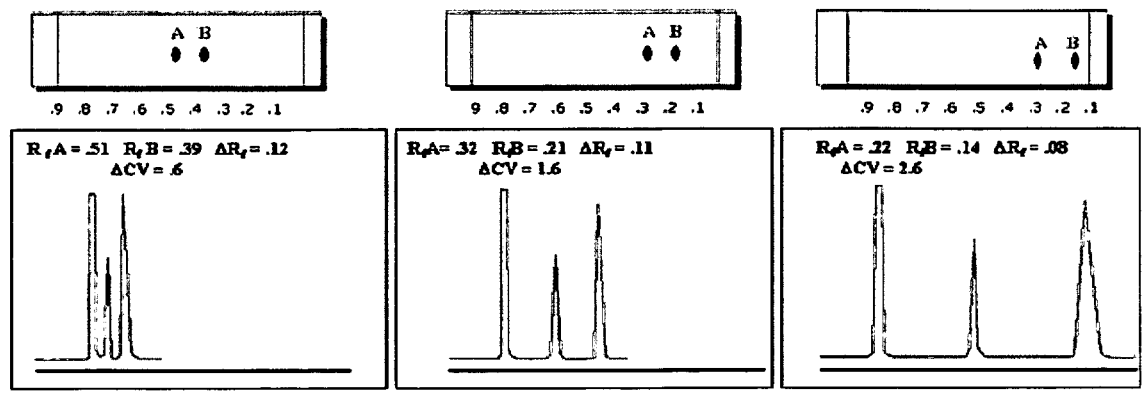
FIG. 8 illustrates the lack of correspondence between $ΔR_f$ data and ΔCV data.

As illustrated in the diagrams provided in FIG. 8, $\Delta CV$ is much more significant with regard to the separation than simple $\Delta R_f$ as a valid indication of the sample load mass that may be adequately separated on a given chromatography system. As shown in the three examples, although the $\Delta R_f$ remained approximately equal (0.12 to 0.08), the resulting $\Delta CV$ values increased, thereby allowing for increasing sample loads improving the ability to separate the components of the sample composition.

This shows that $\Delta CV$ plays a greater role in predicting maximum sample loading than $\Delta R_f$. Accordingly, when considering an increase in the sample loading for a given separation, a number of factors should be taken into account when determining how best to achieve the desired separation including, for example:

1. Alternative solvents and/or gradients that may improve the $\Delta CV$ separation;
2. The $\Delta CV$ of the current solvent system and gradient;
3. The availability of longer columns for improving $\Delta CV$ resolution; and
4. The availability of wider column for increasing sample loading capacity.

The diagrams in FIG. 10A, representing a column loaded with a 1 mg sample (in which $R_{fA}=0.40$, $R_{fB}=0.20$ and $\Delta R_f=0.20$, and FIG. 10B, representing column overloaded with a 10 mg sample (in which $R_{fA}=0.50$, $R_{fB}=0.35$ and $\Delta R_f=0.15$), illustrate the effect of sample mass on the ability of chromatographic systems to resolve the various components present in the sample. This degradation is also reflected in the corresponding TLC results in which the overloaded plate exhibits "tailed" or elongated component regions. These figures illustrate how increased sample loading will reduce the separation resolution that may be achieved and result in poorer separations, i.e., there is increasing overlap in the elution of adjacent compounds as the column is increasingly overloaded.

Column chromatography allows multiple components to be separated and, unlike gravity column chromatography, may reduce the chromatography time by forcing the solvent through the column. The absorbent, typically silica, used in the column are typically provided as relatively small and uniform particles (for example, about the same size as the particles used to form the media layer on TLC plates) that are packed into the column or cartridge to provide a generally uniform density for consistent performance.

Defining a Suitable Solvent System

The initial goal is to identify a solvent system that produces TLC $R_f$ values of between approximately 0.1 and 0.9 on a silica gel plate. For a general separation it may be useful to start with an ethyl acetate-petroleum ether solvent composition. For more strongly polar compounds, acetone (or methylene chloride) and petroleum ether may be a useful starting solvent system. Small amounts of the crude sample material may be dissolved in a minute amount of suitable solvent and applied to a normal-phase silica gel TLC plate without overloading. In the event that the initial solvent system does not provide both a satisfactory $R_f$ value and sufficient separation of the target compound from the adjacent compounds, different solvent combinations should be evaluated until an $R_f$ between about 0.10 and 0.60 is obtained for the target compound. A separation of at least 0.05 $R_f$ between the target compound and the closest adjacent compound on the TLC plate to provide a $\Delta CV$ of at least 0.1 is preferable.

Various considerations come into play when determining the sample loading that may be applied to the column while maintaining acceptable separation performance, including, for example:

Resolution ($\Delta CV$)
  Larger $\Delta CV$=larger loads
Mass ratios
  Overloading of sample prevents distinct separation
  Total loadable mass based on amount of crude sample, not amount of product
Required purity
  Higher purity requirements=lower loads
Required yield
  Higher yield requirements=larger loads
Cartridge size
  Larger cartridges=larger loads.

A number of common solvents may be ranked by their selectivity as indicated below in TABLE 1:

TABLE 1

| Solvent | Selectivity Group |
| --- | --- |
| Diethyl Ether | I |
| Methanol | II |
| Ethanol | II |
| 2-Propanol | II |
| Tetrahydrofuran | III |
| Acetone | VIa |
| Ethyl Acetate | VIa |
| Acetonitrile | VIb |
| Dichloromethane | V |
| Toluene | VII |
| Chloroform | VIII |
| Hexane | — |

Figure 9:
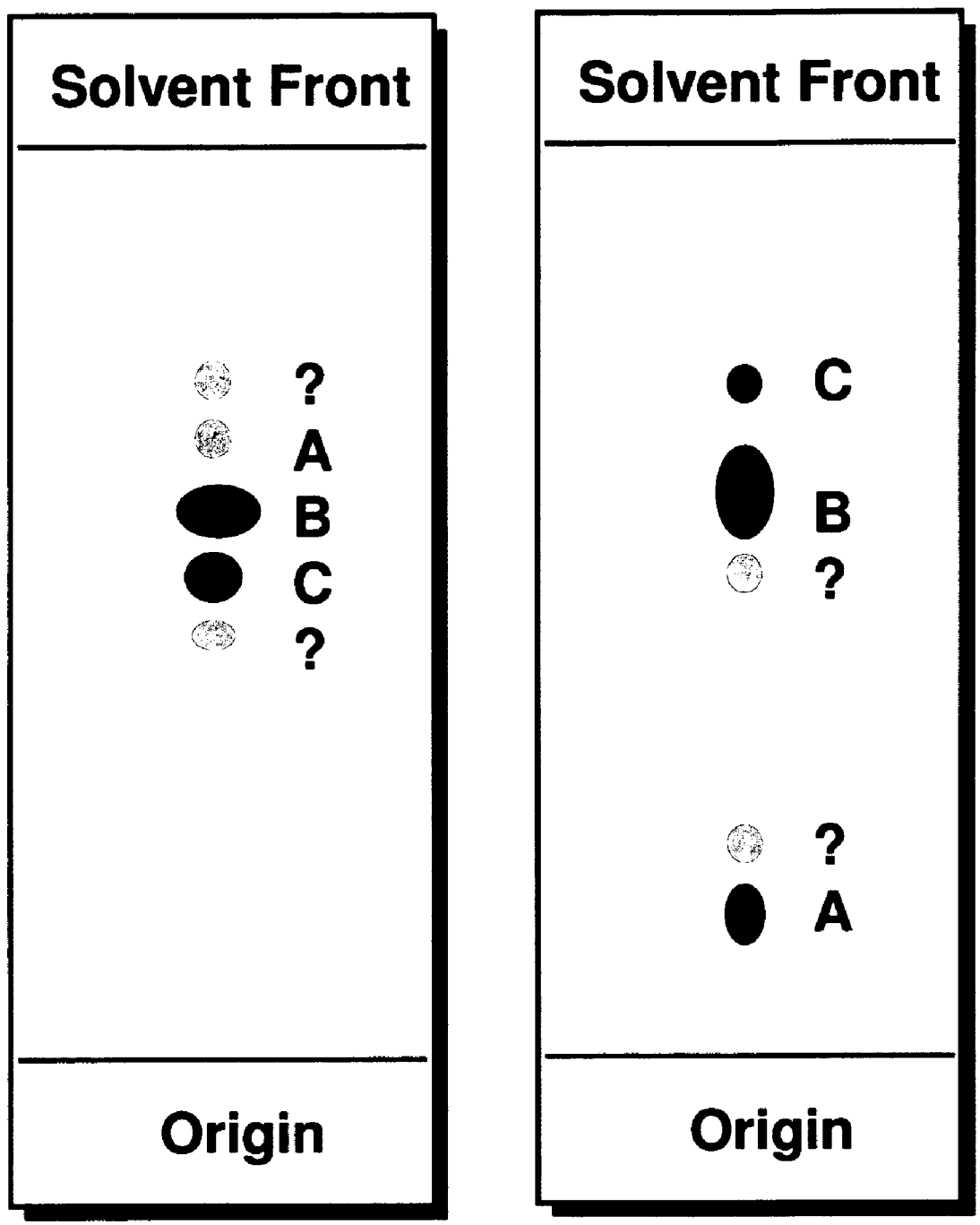
FIG. 9 illustrates the TLC separation of a single sample composition using two different solvent systems.

As indicated in FIG. 9, the selection of the solvent composition for the TLC analysis may produce dramatically different separations for a single sample composition (including known components, A, B and C, and two unknown components, "?".). As will be appreciated by those skilled in the art, the solvent systems that may be utilized in practicing the method according to the invention can include any multi-solvent system in which the various solvent components are miscible over at least the concentration ranges that will be utilized for the separation. In many instances, a solvent system selected from solvents including, but not limited to, methanol, ethanol, 2-propanol, acetonitrile, ethyl acetate, tetrahydrofuran, acetone, dichloromethane, chloroform, diethyl ether, toluene and hexane, will be expected to provide satisfactory results. While in most instances a suitable binary solvent system would be expected to provide satisfactory results, as will be appreciated by those skilled in the art, the system and apparatus may be adapted to accommodate more than two solvents. It is anticipated that in some instances, ternary or quaternary solvent systems may provide certain advantages for the separation of specific classes of compounds or particular target compounds. In other instances, the additional solvent(s) may be used primarily for conditioning the column and/or flushing the column after the compound of interest has been collected and play little or no role in the actual separation. Regardless of how many solvents are incorporated into the solvent system, as noted above, the relative concentrations of the solvents used to form the solvent system should be selected to ensure that the solvents are completely miscible over at least the anticipated working gradient range.

As noted above, flash chromatography has traditionally been used to purify synthetic organic reaction mixtures by isocratic elution where the solvent ratio remains constant throughout the separation. In order to improve the results of such separations, TLC has been used to predict compound elution volume and sample loading for a particular solvent composition.

In flash chromatography, compound retention is typically measured in column volumes (CV), while in TLC, compound retention is typically described or evaluated with reference to a retention factor ($R_f$). Understanding the relationship between $R_f$ and CV, i.e., $CV=1/R_f$, is helpful for understanding and improving flash purification success because this relationship will directly impact compound elution volume and sample load amounts that may be successfully separated using a given column.

For most chemists, this relationship is well understood and has been used routinely in translating TLC $R_f$ data into CV estimates for use with flash chromatography. What has not previously been appreciated is how this relationship between $R_f$ and CV impacts the magnitude of the sample load that may be successfully separated on a given system. Because the CV-$R_f$ relationship is not linear, a simple $\Delta R_f$ is not particularly useful for predicting the separation performance or resolution for a given system, factors which directly impact the acceptable sample loading. The proper isocratic elution load predictor is $\Delta CV$ and based on this sample loading tables have been created and published.

Today, most flash purification is being accomplished by use of gradient elution where the solvent ratio changes over time during the separation process. Because the elution dynamics are different, the isocratic CV-$R_f$ relationship and the loading tables associated with it no longer are valid and chemists must now guess what the sample load should be on any column size and guess what gradient to run to get a separation, reducing the probability of success.

The applicants' continued work in the field has led to an improved method for automatically calculating gradient elution separation parameters and sample load data from the corresponding TLC data (solvents, solvent ratio, $R_f$ values). Experience has shown predictable elution and separation results may generally be obtained by consistently applying a 12 CV concentration gradient based on the TLC separation solvent in which:

the polar solvent component is held at 25% of the TLC separation polar solvent concentration for 1 CV;
the polar solvent component is ramped from 25% of the TLC separation polar solvent concentration to 100% of the TLC solvent ratio over 10 CV; and
the polar solvent component is held at 100% of the TLC separation polar solvent concentration for 1 CV.

For example, if the TLC solvent system's polar solvent concentration was 20%, then the resulting concentration gradient would provide:

5% polar/95% non-polar solvent for 1 CV;
ramp from 5% polar to 20% polar solvent over 10 CV; and
maintain 20% polar solvent for 1 CV.

This basic 3-step approach for developing a concentration gradient works fairly well for compounds eluting between the conventional target $R_f$ values of from about 0.3 to about 0.4 for the target compound, but the relationship between the concentration gradient and the sample loading was not fully appreciated and, consequently, led to instances of both underloading, in which the capacity of the chromatographic system was underutilized, and overloading, in which the capacity of the chromatographic system was exceeded and the target compound(s) were not effectively separated.

For newer generation products, the basic 3-step approach to developing a concentration gradient from TLC data was modified and expanded both to be useful over a broader range of $R_f$ values, for example, 0.1-0.9, and to provide the operators with a reasonable estimate of the sample load capacity for a particular system configuration and solvent system. Extensive experimentation led to a modified 13 CV concentration gradient based on the TLC separation solvent in which:

the polar solvent component is held at 25% of the TLC separation polar solvent concentration for 1 CV;
the polar solvent component is ramped from 25% of the TLC separation polar solvent concentration to 200% of the TLC solvent ratio over 10 CV; and
the polar solvent component is held at 200% of the TLC separation polar solvent concentration for 2 CV.

For example, if the TLC solvent system's polar solvent was again 20%, then the modified concentration gradient would provide:

5% polar/95% non-polar solvent for 1 CV;
ramp from 5% polar to 40% polar solvent over 10 CV; and
maintain 40% polar solvent for 2 CV With this algorithm, an effective concentration gradient may be created for a wide range of TLC polar/non-polar solvent ratios provides a substantially linear relationship between CV and $R_f$ from which $\Delta CV$ and sample load may be determined. This relationship between CV and $R_f$ obtained by using the modified gradient algorithm is reflected in FIG. 7.

To determine the gradient slope, repeated TLC and flash chromatography runs were made using a variety of multi-component samples in solvent systems having non-polar to polar solvent ratios of 9:1, 8:2, 7:3, 6:4, 5:5, 3:1 and 2:1. TLC $R_f$ values were then plotted against actual elution CV from a BIOTAGE™ flash cartridge to generate a graph similar to that illustrated in FIG. 7. The experimental data was then analyzed to derive a linear relationship between CV and $R_f$, the result being expressed as a linear function in slope-intercept form, i.e., equation (I):

$$CV=m(R_f)+b \qquad (I).$$

Initial work with a variety of solvent systems and columns produced the CV-$R_f$ relationship expressed in equation II:

$$CV=-12.264(R_f)+13.431 \qquad (II).$$

Subsequent work with additional solvent systems, sample compositions and sample loadings produced the CV-$R_f$ relationship expressed in equation III.

$$CV=-10.2(Rf)+11 \qquad (III).$$

As reflected in FIG. 7, by applying the modified gradient algorithm a generally linear relationship was obtained between corresponding values of CV and $R_f$. In light of the linear nature of this relationship, the modified gradient algorithm may be extrapolated with high confidence for solvent systems having polar solvent concentrations from about 1% to about 99%. This linear relationship between CV and $R_f$ also makes it possible to provide the operator with an indication of an allowable sample load, in grams, that may be effectively separated on a given system configuration and solvent system based on the TLC data. As will be appreciated by those skilled in the art, repeated trials with a single solvent system, a single column and/or a single sample composition will tend to produce a slightly different CV-$R_f$ relationship than would be obtained with, for example, a different solvent system, different composition, different family of columns or cartridge, or a different solvent gradient. Accordingly, while the general method according to the invention is expected to be suitable in most situations, the degree of precision can be improved by focusing on a reduced operating range if desired in order to tailor the algorithm to a specific application or compound of interest.

Accordingly, for any two $R_f$ values, e.g., the compound of interest and the closest impurity compound detected on the TLC separation, using a non-polar to polar solvent ratio between 99:1 and 1:99, the calculated CV values may be converted to a $\Delta$CV value. For example, suppose a TLC separation performed in a solvent system having a 70:30 non-polar/polar solvent ratio produced an $R_f$ value of 0.6 for the compound of interest and an $R_f$ value of 0.5 for the closest eluting impurity. Applying formula I, the compound of interest has an effective CV of 6.07 while the impurity has an effective CV of 7.3. These two compounds, therefore, have a $\Delta$CV of 1.23 for this particular solvent system.

From data collected using various sample loading studies, a loading table was created, see TABLE 2, which is used to determine the suggested sample load for any given cartridge on the BIOTAGE SP™ systems as a function of the $\Delta$CV achieved between the compound of interest and at least the compound that elutes immediately before or after the compound of interest. As will be appreciated, a similar loading table may be created for any family, collection or assortment of flash chromatography cartridges that will take into account the particular combination of media, cartridge volume and cartridge length using the data from TABLE 2 to guide the experimental design.

various changes in form and details may be made therein without departing from the spirit and scope of the invention as defined by the following claims. In particular, as will be appreciated by those skilled in the art, although the system and method according to the example embodiments of the invention have generally been described in conjunction with a binary solvent system, the system and method are not so limited.

For example, chromatography systems according to the invention may be configured whereby the controller is operatively connected to at least a third solvent supply (and, possibly, a fourth, fifth, etc., solvent supplied) for delivering a range of solvent systems and/or gradients to the inlet for the chromatography column. In one embodiment of the invention, the controller may be configured and operated to supply a solvent gradient in which the concentration of one or more of the miscible solvents is varied over the course of the separation to decrease the effective CV for more slowly eluting compounds.

In another embodiment of the invention, although the bulk of the separation is completed using a binary solvent system, one or more additional solvents may be utilized for conditioning the column before the sample is introduced, flushing the column after the compound of interest has been eluted and/or overlapping with the binary solvent gradient to provide a tertiary, quaternary or higher order solvent system during at least a portion of the separation. For example, in an embodiment in which little or no overlap of the base or primary solvent system, i.e., the solvent system used to construct the solvent gradient that achieves the desired separation, the controller may deliver a flow of a third solvent to the chromatography column before and/or after the period during which the primary solvent system is applied to the column. The primary solvent system and any additional solvents and/or solvent systems may be delivered to the chromatography column in a sequence in which there is substantially no overlap, minimal overlap, partial overlap or substantial overlap between the delivery periods of the various solvents and/or solvent systems as desired.

We claim:

1. A method of separating compounds in a sample using a column chromatography system, the method comprising:
    receiving data input sufficient for determining;

TABLE 2

Gradient loading table.
(Sample Load Mass reported in grams)

| Biotage Cartridge | Effective $\Delta$CV | | | | | | | | | |
|---|---|---|---|---|---|---|---|---|---|---|
| | 0.1-0.4 | 0.5-0.9 | 1.0-1.4 | 1.5-1.9 | 2.0-2.4 | 2.5-3.0 | 3.1-3.5 | 3.6-4.0 | 4.1-5.0 | >5 |
| 12 + S | 0.03 | 0.05 | 0.08 | 0.10 | 0.13 | 0.15 | 0.18 | 0.20 | 0.23 | 0.25 |
| 12 + M | 0.05 | 0.10 | 0.15 | 0.20 | 0.25 | 0.30 | 0.35 | 0.40 | 0.45 | 0.50 |
| 25 + S | 0.13 | 0.25 | 0.38 | 0.50 | 0.63 | 0.75 | 0.88 | 1.0 | 1.1 | 1.3 |
| 25 + M | 0.25 | 0.50 | 0.75 | 1.0 | 1.3 | 1.5 | 1.8 | 2.0 | 2.3 | 2.5 |
| 40 + S | 0.28 | 0.55 | 0.83 | 1.1 | 1.4 | 1.7 | 1.9 | 2.2 | 2.5 | 2.8 |
| 40 + M | 0.55 | 1.1 | 1.7 | 2.2 | 2.8 | 3.3 | 3.9 | 4.4 | 5.0 | 5.5 |
| 65 | 2.0 | 3.9 | 5.9 | 7.8 | 9.8 | 11.7 | 13.7 | 15.6 | 17.6 | 19.5 |
| 75S | 1.2 | 2.4 | 3.5 | 4.7 | 5.9 | 7.1 | 8.2 | 9.4 | 10.6 | 11.8 |
| 75M | 2.0 | 3.9 | 5.9 | 7.8 | 9.8 | 11.7 | 13.7 | 15.6 | 17.6 | 19.5 |
| 75L | 3.9 | 7.8 | 11.7 | 15.6 | 19.5 | 23.4 | 27.3 | 31.2 | 35.1 | 39.0 |

While the invention has been particularly shown and described with reference to example embodiments thereof, it will be understood by those of ordinary skill in the art that at least two retention factors ($R_f$) corresponding to a primary compound and a secondary compound exposed to an initial solvent system; and a proportion of each solvent in the initial solvent system;
generating a solvent ratio profile based on the received inputs including;
    a starting point corresponding to a starting solvent ratio;
    an ending point corresponding to an ending solvent ratio; and
    a transitional phase during which the solvent ratio increases from the starting solvent ratio to the ending solvent ratio; and
introducing separation solvent system having the starting solvent ratio at a solvent flow rate into an upstream end of a chromatography column having a column volume;
introducing a sample including the primary compound and the secondary compound into an upstream end of a chromatography column;
varying the solvent ratio of the separation solvent system being introduced into the upstream end of the chromatography column in accord with the solvent ratio profile; and
carrying at least the primary compound to a downstream end of the chromatography column.

2. The method of separating compounds in a sample according to claim 1, wherein:
the transitional phase has a duration of at least 8 column volumes.

3. The method of separating compounds in a sample according to claim 2, wherein:
the final solvent ratio includes the strong solvent at a solvent concentration of $2C_S$.

4. The method of separating compounds in a sample according to claim 1, wherein:
the initial solvent system includes a strong solvent and a weak solvent, the strong solvent being present at a concentration of $C_S$ in the initial solvent system; and
the starting solvent ratio including the strong solvent at a solvent ratio of $(0.25)C_S$.

5. The method of separating compounds in a sample according to claim 1, wherein:
the initial solvent system includes a strong solvent and a weak solvent, the strong solvent being present at a concentration of $C_S$ in the initial solvent system; and
the final solvent ratio includes the strong solvent at a solvent concentration of $2C_S$.

6. The method of separating compounds in a sample according to claim 1, wherein:
the strong solvent exhibits greater polarity than the weak solvent.

7. The method of separating compounds in a sample according to claim 6, wherein:
the retention factors differ by at least 0.1.

8. The method of separating compounds in a sample according to claim 1, wherein:
at least one retention factor is between 0.1 and 0.9.

9. The method of separating compounds in a sample according to claim 1, wherein:
the separation solvent system solvent ratio varies in substantially linear fashion between the starting solvent ratio and the ending solvent ratio.

10. The method of separating compounds in a sample according to claim 1, wherein:
the separation solvent system solvent ratio varies in a linear fashion between the starting solvent ratio and the ending solvent ratio.

11. The method of separating compounds in a sample according to claim 1, wherein:
the separation solvent system solvent ratio varies in a stepwise fashion between the starting solvent ratio and the ending solvent ratio.

12. The method of separating compounds in a sample according to claim 1, wherein:
the separation solvent system is a solution of miscible solvents.

13. The method of separating compounds in a sample according to claim 1, wherein:
the separation solvent system includes at first solvent from a first selectivity group and a second solvent from a different selectivity group.

14. The method of claim 1 further comprising:
determining a $\Delta$ column volume for the elution of the primary and secondary compounds based on the retention factors.

15. The method of claim 1 further comprising:
determining a sample mass, a column size, and a separation solvent system flow rate to provide a $\Delta$ column volume of at least 0.1 between the primary and secondary compounds.

16. The method of claim 1 further comprising:
determining a sample mass, a column size, and a separation solvent system flow rate to provide a $\Delta$ column volume of at least 0.8 between the primary and secondary compounds.

17. The method of claim 1 further comprising:
determining a $\Delta$ column volume for the elution of the target and adjacent compounds based on the retention factors; and
adjusting the solvent ratio profile to provide a $\Delta$ column volume of at least 0.1 between the primary and secondary compounds.

18. The method of claim 17 further comprising:
determining a target sample loading mass as a function of the $\Delta$ column volume and the chromatography column.

19. The method of claim 17, wherein:
the initial solvent system has a polar/non-polar solvent ratio of 1:99 to 99:1.

20. The method of claim 1, wherein:
the initial solvent system has a polar/non-polar solvent ratio of 1:99 to 99:1.

* * * * *